United States Patent [19]

Briggs et al.

[11] Patent Number: 5,445,959
[45] Date of Patent: Aug. 29, 1995

[54] ENZYME FROM MICROBIAL SOURCE: PHTHALYL AMIDASE

[75] Inventors: Barbara S. Briggs, Indianapolis; Milton J. Zmijewski, Jr., Carmel, both of Ind.

[73] Assignee: Eli Lilly and Company, Indianapolis, Ind.

[21] Appl. No.: 275,488

[22] Filed: Jul. 15, 1994

[51] Int. Cl.[6] ............................ C12N 9/78; C12N 9/80
[52] U.S. Cl. ...................................... 435/228; 435/227
[58] Field of Search ............................... 435/227, 228

[56] References Cited

PUBLICATIONS

Yang et al., *J. Biol. Chem.* 268:10870, 1993.
Kukolja et al., *Croatica Chemica Acta* 49:779, 1977.
Toyoura et al., *Chem. Pharm. Bull.* 7:789, 1959.

*Primary Examiner*—Charles L. Patterson, Jr.
*Assistant Examiner*—Keith D. Hendricks
*Attorney, Agent, or Firm*—Paul R. Cantrell; David E. Boone; Gerald V. Dahling

[57] ABSTRACT

Phthalyl amidase is an enzyme previously unknown in the art that catalyzes removal of the phthalyl moiety from phthalyl-containing amides. The current invention provides said phthalyl amidase, means for producing it by culturing the natural organism from which the activity was identified, and methods for using said phthalyl amidase to remove the phthalyl moiety from phthalyl-containing amides.

5 Claims, 2 Drawing Sheets

ENZYME FROM MICROBIAL SOURCE: PHTHALYL AMIDASE

BACKGROUND OF THE INVENTION

The present invention relates to the discovery of a specific enzyme that has not been previously described, a phthalyl amidase, which readily removes the phthalyl moiety from phthalyl-containing amides. The present invention also relates to an organism isolated from natural sources that produces the enzyme, DNA compounds that encode the enzyme, and methods for producing and using the enzyme.

The phthalimido functional group is an important tool in organic synthesis because of the protection it provides against unwanted reactions. However, dephthalylation reactions generally require harsh conditions and often have low yields thereby limiting the situations in which phthalimido protection can be employed.

Removal of a phthalyl protecting group from a phthalyl amide can be accomplished chemically, Kukolja et al., Croatica Chemica Acta 49:779, 1977, but yields are variable especially with substrates that are unstable to harsh reaction conditions.

Certain enzymes have previously been found that could be used to remove benzoyl groups from benzoylated amino acids. Toyoura et al., Chem. Pharm. Bull. 7:789, 1959. These enzymes were specific for benzoyl groups and for the amino acid to which they were attached. Others have also reported enzymes that will hydrolyze phthalate esters. Kurane et al., Agric, Biolo Chem. 44:529, 1980, However, none of these enzymes have been shown to operate on phthalyl amides.

In contrast, the phthalyl amidase enzyme of this invention catalyzes removal of the phthalyl group from a wide variety of phthalyl-containing compounds with improved yields over processes known in the art, exhibits stereochemical selectivity, and eliminates the need for harsh conditions to remove the protecting group.

SUMMARY OF THE INVENTION

The present invention provides an isolated phthalyl amidase enzyme, which catalyzes the following type of reaction:

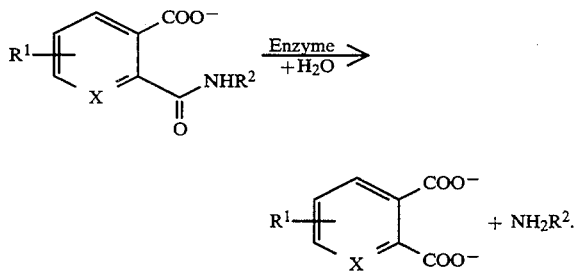

The phthalyl amidase enzyme is characterized by the following:
a) Reactivity: said enzyme catalyzes the removal of the phthalyl group from phthalyl amides generating phthalic acid and an amine;
b) Substrate specificity: said enzyme hydrolyzes phthalylated amino acids, peptides, beta-lactams, aromatic and aliphatic amines; substitutions allowed on the phthalyl group include 6—F, 6—$NH_2$, 3—OH, and a nitrogen in the aromatic ring ortho to the carboxyl group attached to the amine;
c) Reactive pH range: 5.5 to 9.0, with optimum pH of 8.0±0.4;
d) Reactive temperature range: 10° to 50° C., with optimum temperature of 30° C.±4° C. at pH 8.0;
e) Temperature stability: At 200 mM buffer, 80% of enzyme activity retained at 35° C. for 48 hours;
f) Influence of effectors: Iodoacetate, p-HMB, and $Cu^{++}$ exert inhibitory activity;
g) Molecular weight: approximately 49,900 daltons;
h) Subunits: one;
i) Km: 0.9 mM in 50 mM potassium phosphate buffer, 30° C., pH 8.0, when phthalamido carbacephem is the substrate.

The present invention also provides DNA compounds that comprise isolated nucleotide sequences encoding the phthalyl amidase enzyme and methods for expressing such compounds. Preferred DNA compounds comprise an isolated nucleotide sequence encoding SEQ ID NO:2, especially SEQ ID NO:1 isolated from Xanthobacter agilis. Other preferred compounds of the present invention include DNA compounds that comprise isolated DNA sequences encoding the proenzyme form of phthalyl amidase enzyme (SEQ ID NO:4), including SEQ ID NO:3, SEQ ID NO:5, and the phthalyl amidase gene of Xanthobacter agilis (SEQ ID NO:6). DNA compounds of the current invention include recombinant DNA vectors, including expression vectors.

The present invention also provides for DNA sequences of the naturally-occurring phthalyl amidase gene that control transcription, translation, and extra-cellular secretion of proteins. Thus, the present invention includes SEQ ID NO:7, SEQ ID NO:8, and SEQ ID NO:10.

Definitions

Coding sequence—the sequence of DNA in the open reading frame of a gene that encodes the amino acid residue sequence of the protein expressed from the gene.

Gene—a segment of DNA that comprises a promoter, translational activating sequence, coding sequence, and 3' regulatory sequences, positioned to drive expression of the gene product.

Promoter—a DNA sequence that directs or initiates the transcription of DNA.

Recombinant DNA vector—any autonomously replicating or integrating DNA agent, including but not limited to plasmids, comprising a promoter and other regulatory sequences positioned to drive expression of a DNA sequence that encodes a polypeptide or RNA.

Recombinant DNA sequence—any DNA sequence, excluding the host chromosome from which the DNA is derived, which comprises a DNA sequence that has been isolated, synthesized, or partially synthesized.

Restriction fragment—any linear DNA molecule generated by the action of one or more restriction enzymes.

Translation activating sequence—a regulatory DNA sequence that, when transcribed into mRNA, promotes translation of mRNA into protein.

All nucleotide and amino acid abbreviations used in this disclosure are those accepted by the United States Patent and Trademark Office as set forth in 37 C.F.R. §1.822(b)(1993).

BRIEF DESCRIPTION OF THE FIGURES

The restriction enzyme and function maps presented in the drawings are approximate representations of the recombinant DNA vectors discussed herein. The restriction site information is not exhaustive. There may be more restriction enzymes sites of a given type than are actually shown on the map.

DETAILED DESCRIPTION OF THE INVENTION

Figure 1:
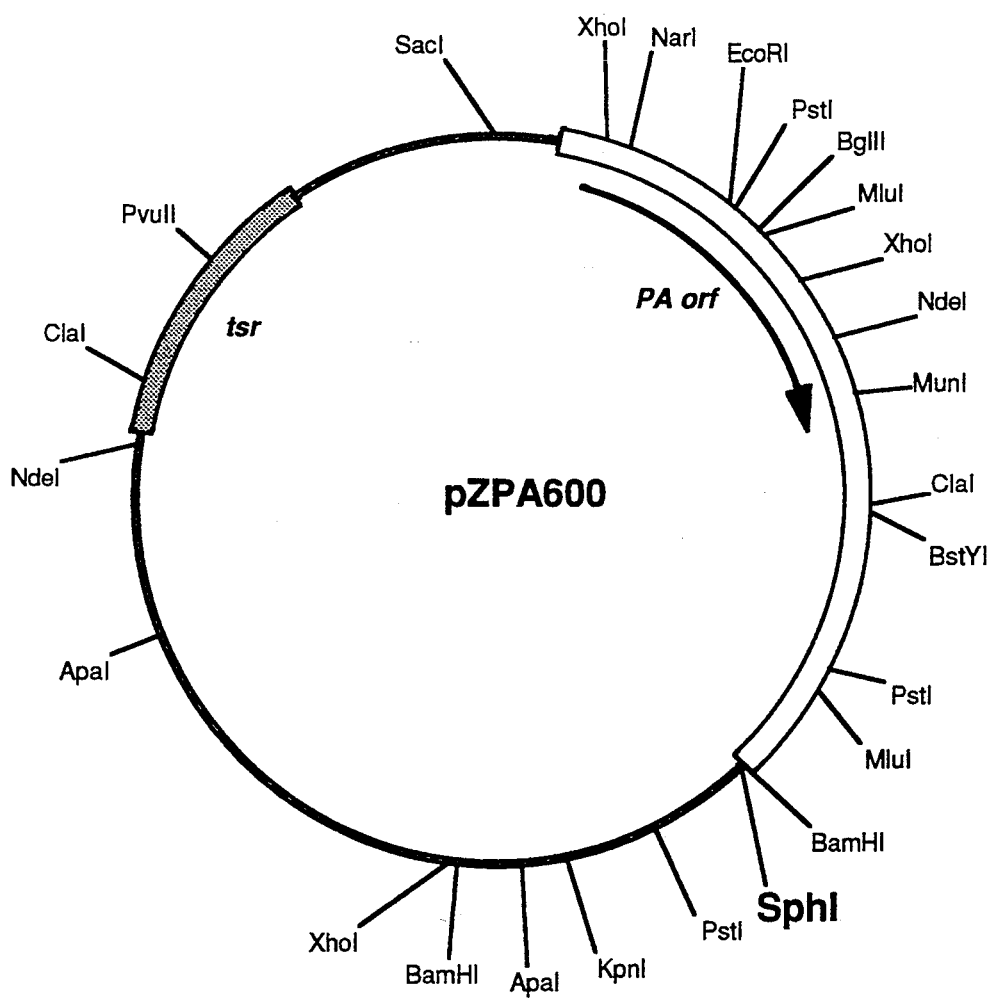
FIG. 1 is a restriction enzyme site and function map of plasmid pZPA600.

During the course of developing a chiral, shorter, and more efficient synthetic route to loracarbef ([6R-(6A,7B(R))]-7-[(aminophenylacetyl)amino]-3-chloro-8-oxo-azabicyclo[4,2,0]oct-2-ene-2-carboxylic acid), the Mitsunobu reaction (see e.g. Hughes, D.L. Organic reactions 42:336, 1992; Bose, A.K. et al., Can. J. Chem. 62:2498, 1984) was selected for forming the beta-lactam ring from a chiral linear amino acid ester intermediate. Several reactants with one N-valence protected and a few reactants with both N-valences protected were examined in Mitsunobu reactions. They were either not cyclized or were cyclized in poor yield.

It was discovered that problems in forming the beta-lactam ring via Mitsunobu reactions could be overcome if both valences of the α-nitrogen of the chiral linear amino acid ester intermediate were protected with a phthalimido group. However, no known chemical reaction was available to remove the phthalimido moiety and regenerate free amine in high yield.

Thus, soil samples were examined for microorganisms that could catalyze removal of the phthalamido group from a test substrate (II) that was formed by base cleavage of the phthalimido ring of a bivalently N-protected compound. A culture was identified that demonstrated phthalyl amidase activity that liberated the free amine derivative of the test substrate. Native enzyme was purified and shown to catalyze the following desired reaction:

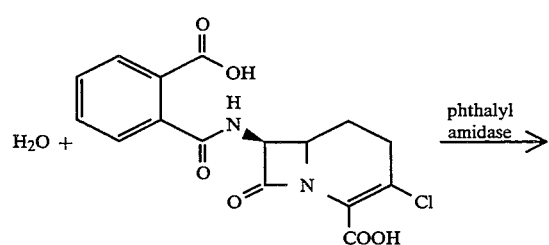

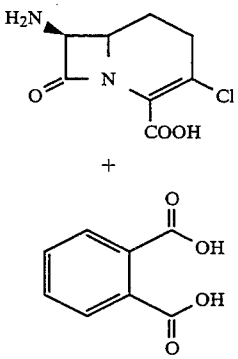

Phthalyl amidase also has significant value in peptide synthesis applications. Phthalimido amino acid derivatives are very effective reactants for enzymatic coupling of amino acids to form peptides. However, heretofore, methods for removing the phthalimido blocking group from the protected peptide were lacking. The phthalyl amidase of the current invention displays reactivity toward a wide range of substrates and can be used for deblocking phthalimido-protected peptide intermediates.

The isolated phthalyl amidase of this invention demonstrates high specific activity toward phthalylated amides or esters (i.e., having a 1,2 dicarboxylate configuration). Such compounds may have other functional groups on the phthalyl aromatic ring and still serve as substrates for the enzyme. For example, acceptable functional groups include 6-F, 6-NH2, and 3-OH. Moreover, substrates may include a nitrogen in the aromatic ring ortho to the carboxyl group attached to the amine. Compounds lacking a 2-carboxylate, such as benzoyl, phenylacetate, phenoxyacetate, or their derivatives, are not substrates for this enzyme.

The enzyme also exhibits a broad substrate specificity in regard to the amine group attached to the phthalate side chain. For example, phthalylated amino acids and peptides, mono- and bicyclic beta-lactams, aromatic and non-aromatic amines, as well as phthalylated amines attached to heterocycles, are dephthalylated by this enzyme at acceptable catalytic rates. The enzyme also removes the methyl group from mono-methyl phthalate.

The enzyme is stable in the broad range of pH from 6–9, having an optimum stability pH of 8.0±0.4. The enzyme also demonstrates a marked stability dependence on ionic strength. Ionic strength above 20 mM enhances pH and temperature stability of the enzyme. Optimum ionic strength occurs at 200 mM and above.

The enzyme retains good activity in low salt (50 mM) up to 30° C. and in high salt (200 mM) up to 40° C. In 200 mM salt, at least 80% of the enzyme activity is retained in temperatures up to 35° C. for 48 hours.

Iodoacetic acid (10 mM), p-HMB (1 mM), and $Cu^{++}$ (1 mM) significantly inhibited the enzyme. No organic cofactors, such as ATP, NADPH, or others, stimulated enzyme activity. EDTA, phenanthroline, and metal ions besides $Cu^{++}$ had little or no effect on enzyme activity.

The molecular weight of the enzyme is approximately 49,900, as determined by electrospray mass spectrometry, and the molecule consists of one subunit.

The $K_m$, with phthalamido carbacephem (7-phthalamido-3-chloro-4-carboxy-1-carba-dethioceph-3- em) (III) as substrate, is 0.9 mM in 50 mM potassium phosphate buffer, pH 8.0, and 30° C. The $V_{max}$ for this substrate and under these conditions is 7.6 μmol/min/mg.

Phthalyl amidase activity was recovered from a microorganism isolated from soil samples. The organism was characterized by comparison of its fatty acid methyl ester profile with that of known standards, and has been identified as a strain of Xanthobacter agilis.

The organism can be preserved as lyophilized culture and has been deposited with the National Center for Agricultural Utilization Research, 1815 North University Street, Peoria, Ill. 61604-39999, under accession number NRRL B-21115 (date of deposit: Jun. 28, 1993). Working cultures are maintained as liquid cultures stored in liquid nitrogen or at temperatures below −78° C.

In order to recover the phthalyl amidase of this invention, Xanthobacter agilis can be cultivated in an aqueous nutrient medium consisting of a source of carbon and nitrogen and mineral salts at an initial pH between 6 and 8 and at 25° to 37° C. A number of agents can be included in the culture medium as inducers of enzyme production, including, for example, phthalate (PAA), phthalyl glycine (PAG), and phthalyl monocyclic beta-lactam (PMBL). The enzyme can be recovered in larger amounts by cultivating Xanthobacter agilis in a known manner in a bioreactor of desired size, for example, with a working volume of 100 liters. Good aerating conditions, and the presence of nutrients in complex form, and a pH between 6 and 8 are important for a successful culture. The cell mass can be separated from the medium and the enzyme purified as shown in Example 4.

It will be recognized by those skilled in the art that phthalyl amidase-producing mutants of the isolated Xanthobacter agilis organism can readily be made by methods known in the art. These mutants are considered within the scope of this invention.

As described, phthalyl amidase, catalyzes the removal of the phthalyl moiety from a wide range of phthalimido-containing compounds. The enzyme actually cleaves the amide bond of a phthalamido substrate, which is formed by the action of mild base on the corresponding phthalimido compound. This conversion proceeds readily under conditions that are suitable for enzyme activity. Thus, the phthalimido-containing compound and the enzyme being concurrently present under conditions that promote enzyme activity result in in situ removal of the phthalyl group.

In some chemical reactions involving an amine reactant, the corresponding phthalimido compound is particularly suited to high reaction yields whereas the conversion proceeds poorly with the unprotected amine or with a monovalently protected amine or even when the amine is bivalently protected by an alternative means. Thus, the current invention, which provides an economic source of phthalyl amidase, allows practical synthesis of a variety of amine products via phthalimido-protected amine intermediates.

It will be recognized that the enzyme can also be used in immobilized form to catalyze desired reactions according to procedures known in the art.

A specific application of the current invention occurs in a new chiral synthesis of the antibiotic loracarbef. The phthalyl amidase-catalyzed reaction shown above is one step of that synthesis.

Another application occurs in the synthesis of aspartame (N-L-α-aspartyl-L-phenylalanine, 1-methyl ester) as described in Example 16 below.

In both cases phthalic anhydride (or other suitable activated forms of phthalic acid) is used to react with an intermediate containing a key amino group so that a phthalimido moiety is formed for bivalent protection of the amino group. The bivalently protected amine can then be converted efficiently to a desired intermediate. For example, cyclization of a α-phthalimido-β-hydroxy-acid to a beta-lactam, or for example, condensation of an α-phthalimido carboxy-activated amino acid with a carboxy-protected amino acid to form a dipeptide. The phthalimido moiety is hydrolyzed with mild base and the resulting phthalamido moiety is then exposed to phthalyl amidase to catalyze the removal of the phthalyl moiety and release free amine plus phthalic acid.

In addition to identification and isolation of a naturally-occurring phthalyl amidase, the current invention provides DNA compounds that comprise an isolated nucleotide sequence encoding phthalyl amidase, recombinant DNA vectors encoding phthalyl amidase, host cells transformed with these DNA vectors, and a method for producing recombinant phthalyl amidase. These elements of the current invention provide the opportunity to use phthalyl amidase as a biocatalyst in industrial scale chemical processes°

Phthalyl amidase may be produced by cloning DNA encoding phthalyl amidase into a variety of vectors by means that are well known in the art. A number of suitable vectors may be used, including cosmids, plasmids, bacteriophage, and viruses. One of the principle requirements for such a vector is that it be capable of reproducing itself and transforming a host cell. Preferably, the vector will be a recombinant DNA vector that is capable of driving expression of phthalyl amidase encoded by the DNA compounds of this invention. Typical expression vectors comprise a promoter region, a 5'-untranslated region, a coding sequence, a 3'-untranslated region, an origin of replication, a selective marker, and a transcription termination site.

After the DNA compound encoding phthalyl amidase has been inserted into the vector, the vector may be used to transform a host cell. In general, the host cell may comprise any cellular organism, including a prokaryotic cell or eukaryotic cell, that is capable of being transformed with a vector comprising the DNA of this invention. The techniques of transforming and transfecting cells are well known in the art and may be found in such general references as Maniatis, et al. (1989) or Current Protocols in Molecular Biology (1989).

A particularly preferred method of the current invention generates soluble, extra-cellular enzyme. The method makes use of a DNA compound that comprises SEQ ID NO:6, which enables, when transformed into Screptomyces lividans as part of a self-replicating vector, the host to produce and secrete soluble mature phthalyl amidase in an amount 20-fold in excess of the amount of a cell-bound form of the enzyme produced by Xanthobacter agilis, the bacterium from which the DNA compound was cloned.

SEQ ID NO:6 comprises four functional components: SEQ ID NO:7; SEQ ID NO:8; SEQ ID NO:1; and SEQ ID NO:10. SEQ ID NO:7, which includes the promoter-bearing nucleotides 1–135 of SEQ ID NO:6, promotes transcription of the coding sequences. SEQ ID NO:8 (nucleotides 136–261 of SEQ ID NO:6) encodes the signal peptide portion of a proenzyme form of phthalyl amidase (pro-phthalyl amidase (SEQ ID NO:4)). The signal peptide (SEQ ID NO:9), which provides for transport of the proenzyme across the microbial cell wall of Streptomyces lividans, is cleaved from the proenzyme by the cell, thereby enabling extracellular production of the mature enzyme. SEQ ID NO:1 (nucleotides 262–1620 of SEQ ID NO:6) encodes mature phthalyl amidase (SEQ ID NO:2). SEQ ID NO:10 (nucleotides 1621–3029 of SEQ ID NO:6) is a 3'-untranslated region which assists proper and efficient translation termination of the mRNA that encodes pro-phthalyl amidase.

Moreover, in a more general application of the expression method of the current invention, a wide variety of soluble, extra-cellular, properly-folded, functional proteins may be produced in Streptomyces. The current method comprises propagating Streptomyces lividans that has been transformed with a DNA compound, which encodes the desired enzyme, protein, or peptide, and which includes the transcriptional and translational regulatory elements of the phthalyl amidase gene isolated from the bacterium Xanthobacter agilis. These regulatory elements enable synthesis and secretion of the soluble, properly-folded, functional enzyme, protein, or peptide.

To accomplish the general method, the DNA sequence encoding mature phthalyl amidase (SEQ ID NO:1) may be replaced in SEQ ID NO:6 by a heterologous open reading frame from a wide variety of organisms wherein the heterologous open reading frame encodes a mature protein or hormone and introns are absent from those open reading frames, either by nature or by virtue of precise removal from genomic DNA to form cDNA open reading frames. In this arrangement, the regulatory elements of the phthalyl amidase gene continue to function such that proteins and oligopeptides other than phthalyl amidase are produced and secreted from Streptomyces transformed with the modified DNA sequence. Thus, substitution of a desired protein-encoding sequence for the coding sequence of mature phthalyl amidase enables economic extra-cellular production of numerous enzymes, peptides, and peptide hormones.

Synthesis of the phthalyl amidase gene and its various elements can be accomplished by recombinant DNA technology. Synthetic genes, the in vitro or in vivo transcription and translation of which will result in the production of the phthalyl amidase enzyme, may be constructed by techniques well known in the art. Owing to the degeneracy of the genetic code, the skilled artisan will recognize that a sizable, yet definite, number of DNA sequences may be constructed, which encode the phthalyl amidase enzyme. All such sequences are provided by the present invention.

A preferred sequence encoding phthalyl amidase is the naturally-occurring phthalyl amidase gene of Xanthobacter agilis, which is SEQ ID NO:6. This preferred gene is available on an 3.2 kb SacI-BamHI restriction fragment of plasmid pZPA600, which can be isolated from Streptomyces lividans TK23/pZPA600 by techniques well known in the art. Streptomyces lividans TK23/pZPA600 designates Streptomyces lividans strain TK23 which has been transformed with vector pZPA600.

Plasmid pZPA600 was derived by ligating SEQ ID NO:6 into Streptomyces vector, pIJ702 (Hopwood, D.A., Bibb, M.J., Smith, C.P., Ward, J.M., Schremph, H., Genetic Manipulations of Streptomyces: A Laboratory Manual, The John Innes Foundation, Norwich, England, 1985). The pIJ702 vector contains a pIJ101 Streptomyces replicon and a thiostrepton resistance gene for selection. The ligated material was transformed into Streptomyces lividans TK23 by a standard protoplast fusion technique. After selection on thiostrepton (45 mg/ml), the plasmid designated pZPA600, was isolated and confirmed by restriction analysis. A restriction site and function map of plasmid pZPA600 is found in FIG. 1.

Streptomyces lividans TK23/pZPA600 is publicly available and on deposit at the National Center for Agricultural Utilization Research, 1815 North University Street, Peoria, Ill. 61604-39999, under accession number NRRL B21290 (date of deposit: Jun. 23, 1994). The Streptomyces lividans TK23 strain has been previously described in Plasmid 12:1936 (1984).

Plasmid pZPA600 allows high level expression of the pro-phthalyl amidase open reading frame and results in secretion of soluble mature phthalyl amidase, which process is especially preferred. Thus, the invention comprises a process in which Streptomyces lividans TK23/pZPA600 is grown and then separated from its extra-cellular broth so that high concentrations of phthalyl amidase are obtained in that cell-free broth.

Other preferred sequences include, for example, SEQ ID NO:i, which encodes mature phthalyl amidase enzyme (SEQ ID NO:2), and SEQ ID NO:3, which encodes the proenzyme form of phthalyl amidase (SEQ ID NO:4). Thus, the present invention also comprises plasmid pZPA400 as a preferred embodiment.

Figure 2:
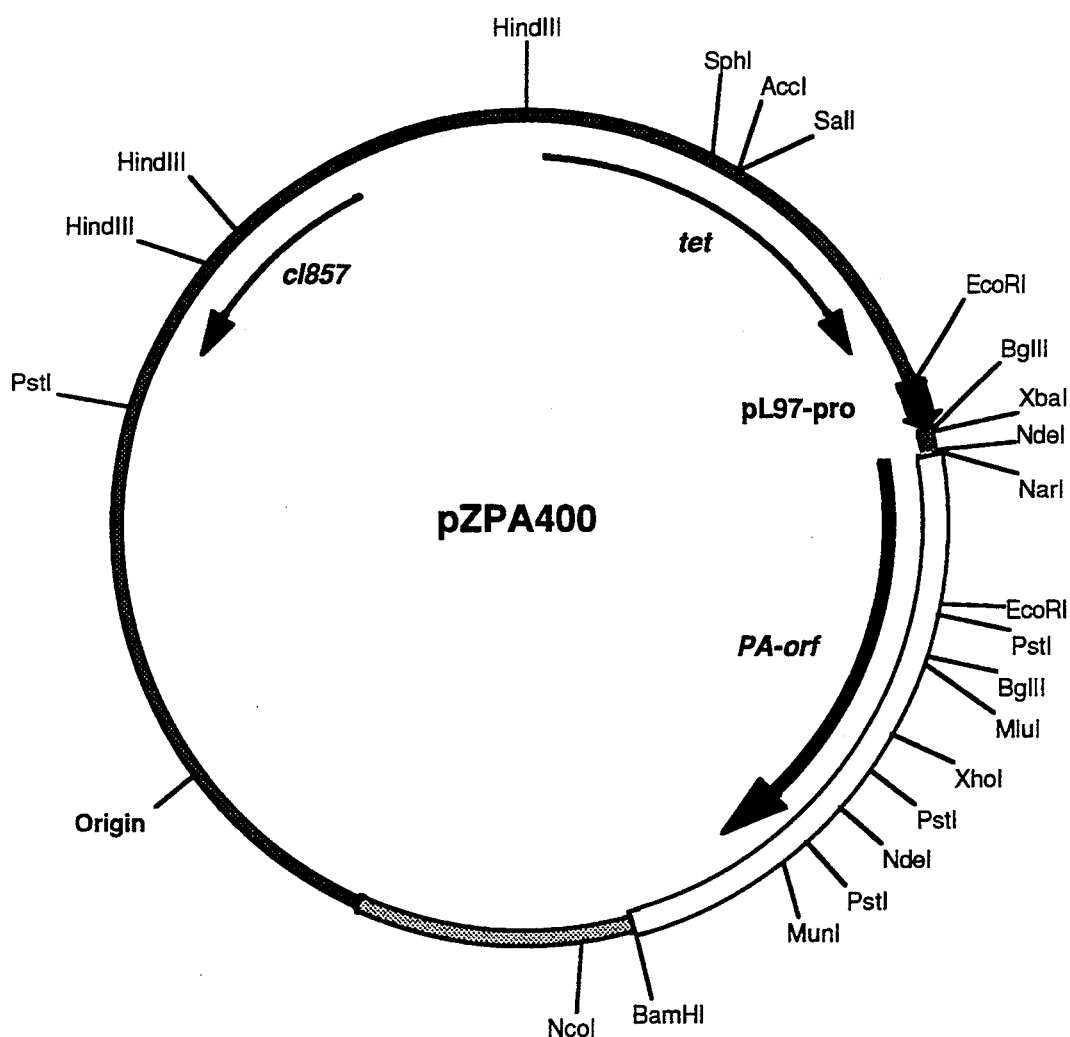
FIG. 2 is a restriction enzyme site and function map of plasmid pZPA400.

In plasmid pZPA400, the regulatory elements of the native gene were removed and a methionyl residue was attached to the 5'-terminal nucleotide of the mature phthalyl amidase coding sequence to generate an open reading frame (SEQ ID NO:11) encoding met-phthalyl amidase (SEQ ID NO:12). This sequence was positioned, via a two-cistron configuration, to be driven by a temperature inducible lambda pL promoter. Plasmid pZPA400 also contains the temperature sensitive cI857 repressor gene, a tetracycline resistance gene, and the pBR322-based origin of replication minus the rop region, which controls copy number (Cesareni et al., Proc. Natl. Acad. Sci. 79:6313, 1982). E. coli cells harboring this plasmid (E. coli DH5α/pZPA400) are induced to produce met-phthalyl amidase (without signal peptide) when the culture temperature is raised from 30° C. to 42° C. A restriction site and function map of plasmid pZPA400, which can be isolated from E. coli DH5α/pZPA400 cells by techniques well known in the art, is found in FIG. 2.

E. coli DH5α/pZPA400 designates the commercially available E. coli DH5α strain that has been transformed with plasmid pZPA400. Es coli DH5α/pZPA400 cells are publicly available and on deposit at the National Center for Agricultural Utilization Research, 1815 North University Street, Peoria, Ill. 61604-39999, under accession number NRRL 21289 (date of deposit: Jun. 23, 1994).

The phthalyl amidase gene may also be created by synthetic methodology. Such methodology of synthetic gene construction is well known in the art. See Brown et al. (1979) Methods in Enzymology, Academic Press, N.Y., 68:109. The phthalyl amidase DNA sequence may be generated using a conventional DNA synthesizing apparatus, such as the Applied Biosystems Model 380A of 380B DNA synthesizers (commercially available from Applied Biosystems, Inc., 850 Lincoln Center Drive, Foster City, Calif. 94404.

Synthesis of the phthalyl amidase protein of the present invention may also proceed by solid phase synthesis. The principles of solid phase chemical synthesis of polypeptides are well known in the art and may be found in general texts, such as, Dugas, H. and Penny, C., Bioorganic Chemistry (1981), Springer-Verlag, N.Y., pp. 54-92. However, recombinant methods are preferred if a high yield is desired.

A skilled artisan will recognize that the nucleotide sequences described in the present disclosure may be altered by methods known in the art to produce additional sequences that substantially correspond to the described sequences without changing their functional aspects. These altered sequences are considered to be included in the current invention.

In order that the invention described herein may be more fully understood, the following examples are set forth. It should be understood that the examples are for illustrative purposes only and are not to be construed as limiting the scope of the invention.

EXAMPLE 1

Search for phthalyl amidase producing organisms 240 soil samples (8 to 15 mg of damp dry soil) were individually suspended in 10 ml sterile BL medium (hereinafter defined) containing 100 mg phthalyl monocyclic beta-lactam (PMBL) (I).

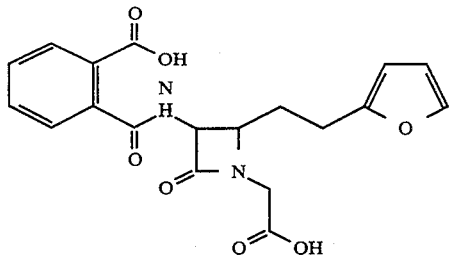

Bl medium had the following composition:

| | | |
|---|---|---|
| Na$_2$HPO$_4$ | 6.0 | g |
| KH$_2$PO$_4$ | 3.0 | g |
| NaCl | 0.5 | g |
| NH$_4$Cl | 2.0 | g |
| CaCl$_2$ | 0.1 | g |
| MgSO$_4$.7H$_2$O | 0.25 | g |
| ZnSO$_4$.7H$_2$O | 70 | mg |
| FeCl$_3$.6H$_2$O | 270 | mg |
| MnSO$_4$ | 80 | mg |
| CuCl$_2$ | 7.4 | mg |
| CoSO$_4$.7H$_2$O | 28 | mg |
| H$_3$BO$_3$ | 3 | mg |
| Yeast Extract | 1.0 | g |
| Deionized water | 1.0 | L |
| pH | 7.0 | |

The cultures were incubated aerobically at 30° C. in a rotary shaker at 250 rpm for as long as 2 weeks. Cultures were examined by thin layer chromatography at 7 day intervals for the disappearance of the starting substrate and appearance of the beta-lactam nucleus product.

A culture showing the desired catalytic activity was transferred at least two more times under similar conditions of medium and growth. The final culture was diluted with sterile water and plated out on agar plates containing either Trypticase Soy Broth (Difco) or Bac MI medium. Bac MI medium had the following composition:

| | |
|---|---|
| Peptone | 10.0 g |
| Beef Extract | 5.0 g |
| Yeast Extract | 2.0 g |
| NaCl | 5.0 g |
| Deionized water | 1.0 L |
| pH | 7.0 |

(Agar plates were prepared by adding 20 g agar per L of medium).

Individual colonies were picked from the agar and grown in Bac Ml medium containing 10 mg/ml of PMBL for 12 days at 30° C. with aeration. Broths were examined for appearance of beta-lactam nucleus and phthalic acid using TLC.

A pure isolated organism that demonstrated rapid hydrolysis of the substrate was then grown in Bac MI medium containing 1 mg/ml phthalate for 48 hours at 30° C. with aeration. Cells were centrifuged and then suspended in 50 mM Tris-HCl buffer, pH 8.0, at a ratio of 1 g wet weight cells to 8 ml of buffer. A solution of lysozyme, 2 mg in 1.0 ml 50 mM EDTA, pH 8.2, was added at the ratio of 1 ml lysozyme solution to 8 ml cell suspension. After mixing well and holding at room temperature for 1 hour, the suspension was cooled to 4° C. and held overnight. The resultant viscous solution was sonicated only long enough to liquefy the solution. This solution was centrifuged at 10,000 rpm for 15 minutes. The pellet was discarded and the supernatant tested for phthalyl amidase activity.

The cell-free extract was chromatographed on a size exclusion column (1.5×100 cm; Sephacryl S-300; Pharmacia, Piscataway, N.J.) at 4° C. with an elution buffer consisting of 50 mM potassium phosphate and 150 mM KCl at a flow rate of 0.5 ml/min. The eluant was monitored at a wavelength of 280 nm. UV-absorbing fractions were tested for hydrolysis of PMBL by HPLC.

Reference proteins for molecular weight (daltons) determination were chymotrypsinogen (25,000), ovalbumin (43,000), albumin (67,000), aldolase (158,000), catalase (232,000), ferritin (440,000), and thyroglobulin (669,000).

Cell-free extract of the organism subsequently identified as Xanthobacter agilis was determined to contain an enzyme that catalyzed the hydrolysis of PMBL, and which had an approximate molecular weight of 54,000 daltons and a specific activity of 39.7 nmol/min/mg.

EXAMPLE 2

Production of phthalyl amidase from Xanthobacter agilis

Fermentation of Xanthobacter agilis on a 100 L scale was conducted in 100 L working volume bioreactors, with automatic control for pH (7.9-8.1), temperature (30° C.), air flow (1 scfm), agitation (300 rpm), and back pressure (5 lb). Dissolved oxygen levels (>50%) were kept constant by small increases in agitation speed. The medium consisted of 1.25% Bacto peptone, 0.3% yeast extract, 0.5% beef extract, 0.5% phthalic acid, 0.5% NaCl, and 0.05% anti-foam. After sterilization, the medium was brought to pH 8.0 with 30% sulfuric acid. The fermenter was inoculated with 1 L of pre-culture which had been incubated at 30° C. for 24 hours in the same medium with shaking at 300 rpm. After 48 hours of growth, the fermentation broth was cooled and centrifuged at 17,000 rpm with a flow rate of 1 to 2 L/min to remove the biomass. The cell paste was harvested and stored at −20° C. yielding 6.0 g wet cell weight/L.

EXAMPLE 3

Induction of Phthalyl Amidase

Three compounds at different concentrations were added to aerated cultures of the organism growing at 30° C. in Bac MI medium. The compounds tested were phthalate (PAA), phthalyl glycine (PAG), and PMBL. Cells of Xanthobacter agilis were grown with aeration for 24 hours. This vegetative culture was used to inoculate Bac MI medium (50 ml) containing different concentrations of the compounds to be tested. After 48 hours growth under standard conditions, cells were harvested by centrifugation and wet weight of the cells was determined. Crude cell extracts were prepared by lysozyme treatment of the cells as in Example 1. Suspensions were briefly sonicated to break up the viscous suspension, A cell-free supernatant was obtained by centrifugation of the suspension at 14,000 rpm for 15 minutes.

Enzyme activity in cell-free lysates was determined by monitoring conversion of the chromogenic substrate 4-(2'-carboxy-N-benzoyl)amino-2-carboxy-nitrobenzene (II) to 2-nitro-5-amino benzoic acid and phthalic acid, a reaction catalyzed by phthalyl amidase as shown below:

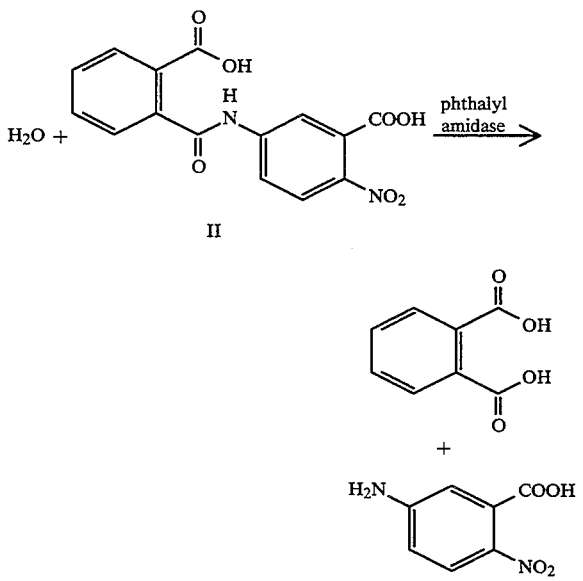

The assay reaction mixture (1 ml) consisted of 0.3 μmol of the chromogenic substrate (II) and 0.001–0.5 μg of enzyme preparation in 50 mM potassium phosphate buffer, pH 8.0 (buffer A). The enzymatic reaction was conducted at 30° C. for 10 minutes and the appearance of product was monitored at 380 nm (or 430 nm). The amount of substrate hydrolyzed was calculated from a standard curve of the amine product.

As can be seen in Table 1, PAG and PAA increased the wet weight cell mass while PMBL had no effect. However, all three substrates produced a dramatic concentration-dependent increase in the total number of enzyme units recovered. The units of enzyme per gram of wet weight cells also increased with all additions but the increase was most pronounced at high PAA concentrations.

TABLE 1

| Inducer | Addition (mg/ml) | Cell weight (g/50 ml) | Total units/ mg protein (μmol/min/mg) | Units/ g cells |
|---|---|---|---|---|
| Control | — | 0.29 | 0.017 | 0.06 |
| PAG | 1 | 0.33 | 0.35 | 1.04 |
|  | 5 | 0.5 | 4.4 | 9.4 |
| PMBL | 1 | 0.35 | 0.28 | 0.79 |
|  | 5 | 0.24 | 2.0 | 8.1 |
| PAA | 1 | 0.35 | 1.4 | 3.9 |
|  | 2 | 0.47 | 4.3 | 9.3 |
|  | 5 | 0.7 | 3.7 | 5.5 |
|  | 10 | 0.6 | 12.0 | 19.8 |

EXAMPLE 4

Purification of Phthalyl Amidase

A. Analytical scale purification of phthalyl amidase

Cells of Xanthobacter agilis (200 grams, wet weight), which contained significant amounts of phthalyl amidase activity, were resuspended to 1800 ml in 50 mM Tris-HCl, pH 8.0, plus 5 mM EDTA. The cells were broken by sonication for 22 minutes at a maximal power below 8° C. DNase (1 μg/ml) and magnesium sulfate (10 mM) were added during the sonication to minimize viscosity and improve cell breakage. After a high-speed centrifugation, the resulting crude extract supernatant served as the source for further enzyme purification. All subsequent purification steps were conducted at 4° C.

The crude extract was loaded onto a Q-Sepharose column (4.4×23 cm; Pharmacia), previously equilibrated with buffer A. After washing with buffer A, a linear gradient of 0–1.5 M KCl in buffer A was applied and the phthalyl amidase eluted as a single activity peak between 1 and 1.1 M KCl. Selected fractions containing most of the enzyme activity were pooled as Q-Sepharose eluate.

The Q-Sepharose eluate was subjected to ammonium sulfate fractionation. The majority of the enzyme activity was recovered from 67–77, 77–87 and 87–97% ammonium sulfate pellets. Those pellets were solubilized in buffer A with 0.2 M ammonium sulfate.

Ammonium sulfate was added to the 67–97% ammonium sulfate enzyme pool to a final concentration of approximately 2 M. The enzyme pool was loaded onto a Phenyl-Sepharose column (2.6×16 cm; Pharmacia), which was previously equilibrated with buffer A plus 2.6 M ammonium sulfate. The phthalyl amidase eluted with a linear gradient decreasing from 2.6 M to 0 M ammonium sulfate in buffer A as a single activity peak between 0 M and 0.5 M ammonium sulfate. Selected fractions containing the majority of the enzyme activity were pooled as Phenyl-Sepharose eluate.

The Phenyl-Sepharose eluate was dialyzed against buffer A and then loaded onto a hydroxylapatite column (1.5×90 cm; Clarkson Chemical Company, Williamsport, Pa.), which was previously equilibrated with buffer A. After washing the column with buffer A, the enzyme eluted with a linear gradient of 50–500 mM potassium phosphate, pH 8.0, as a single activity peak between 150 and 190 mM potassium phosphate. Selected fractions containing most of the enzyme activity were pooled as hydroxylapatite eluate.

After a dilution of the buffer strength from 120 to 50 mM potassium phosphate, the hydroxylapatite eluate was loaded onto a Mono P column (0.5×20 cm; Pharmacia), which was previously equilibrated with buffer A. After washing with 3 column volumes of buffer A, a linear gradient of 0–1.5 M KCl in buffer A was applied and the enzyme eluted as a single activity peak between 0.72 and 0.8 M KCl. Those fractions containing the majority of the enzyme activity were pooled as Mono P eluate. The most active enzyme preparation was derived from Mono P FPLC (Fast Protein Liquid Chromatography).

Table 2 summarizes the results of the purification. Based on sodium dodecyl sulfate-polyacrylamide gel electrophoresis (SDS-PAGE) and Laser Densitometric Scanning, the phthalyl amidase was greater than 95% pure.

The phthalyl amidase activity reported in Table 2 was determined using the chromogenic substrate as in Example 3. A typical reaction mixture in a total volume of 1 ml contained 0.2 mg of the chromogenic substrate and an aliquot of phthalyl amidase in buffer A. The enzymatic reaction was conducted at 30° C. for 10–15 min. Formation of the reaction product was monitored with a spectrophotometer at 430 nm (or 380 nm) and quantitated from a standard curve of the product.

TABLE 2

| Step | Protein (mg) | Activity (Units) | Spec. Act. (Units/mg) | Purification (fold) | Yield (%) |
| --- | --- | --- | --- | --- | --- |
| Crude Extract | 5475 | 345 | 0.063 | 1 | 100 |
| Q Sepharose | 230 | 279 | 1.214 | 19 | 81 |
| Ammonium Sulfate: 67–97% cut | 145 | 224 | 1.547 | 25 | 65 |
| Phenyl-Sepharose | 63 | 158 | 2.505 | 40 | 46 |
| Hydroxyl-apatite | 28 | 154 | 5.52 | 88 | 45 |
| Mono P | 16.5 | 119 | 7.2 | 119 | 34 |

B. Preparative Scale Purification of Phthalyl Amidase

Crude extract of Xanthobacter agilis was prepared by adding 1 g of cells (wet weight) and 2 mg lysozyme per 9 ml of 50 mM Tris-HCl buffer, pH 8.0, 1 mM EDTA (600 g cells total). After 30 minutes at room temperature, DNase (100 U/g of cells) in 10 mM magnesium sulfate was added. The cells were homogenized using a cell homogenizer for 30 minutes at room temperature. After 17 hours of incubation at 8° C., the lysate was centrifuged at 10,000 rpm for 30 minutes.

The crude extract supernatant (4.5 L) was applied to a Super-Q column (7×40 cm; TosoHaas, Montgomeryville, Pa.) equilibrated in buffer A. After loading crude extract, the column was washed with 2 column volumes of 50 mM phosphate buffer containing 3.5 M urea, pH 8.0. A second wash (5 L) was used to re-equilibrate the column in buffer A. Phthalyl amidase eluted from the column using a 10 column-volume linear gradient of 0–1.5 M KCl in buffer A. Fractions were collected and assayed for enzyme activity. The active fractions were pooled (1.5 L), concentrated (250 ml), and diafiltered with buffer A at 7°–10° C.

The concentrated and diafiltered Super-Q mainstream was applied to a hydroxylapatite column (3.2×40 cm) equilibrated in buffer A. After washing the column with this buffer, phthalyl amidase was eluted using a linear gradient of 0–500 mM phosphate buffer, pH 8.0. Fractions were assayed according to the chromogenic substrate method (see Example 3) and the active fractions were pooled (1 L) and concentrated (400 ml).

Table 3 shows the results of this purification.

TABLE 3

| Step | Activity (Units) | Spec. Act. (Units/mg) | Purification (Fold) | Yield (%) |
| --- | --- | --- | --- | --- |
| Crude Extract | 14,846 | 0.8 | 1 | 100 |
| Super-Q | 6,828 | 3.0 | 4 | 46 |
| Hydroxyl-apatite | 4,985 | 9.0 | 11 | 34 |

EXAMPLE 5

Effect of pH on Phthalyl Amidase Activity

The effect of pH on the reaction rate of the analytical scale purified enzyme was determined using phthalamido carbacephem (III) as substrate.

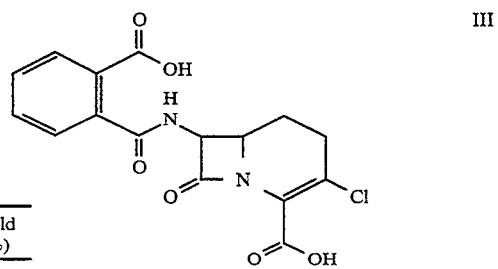

III

A typical reaction mixture consisted of 1 ml total volume and contained 0.1 mM III, 0.1 μM phthalyl amidase in 50 mM potassium phosphate buffer (pH 5.5–9.0) at 2° C. for 20 minutes. The reactions were stopped by the addition of 1 ml methanol. After removal of precipitate by centrifugation, an aliquot of the supernatant fraction (typically 30 μl) was monitored for the beta-lactam nucleus and phthalic acid by HPLC using a Zorbax C8 column (0.46×15 cm; MacMod Analytical Inc., Chadds Ford, Pa.). The two reaction products were eluted by a mobile phase constructed as continuous mixed gradients from (a) 1% ACN (acetonitrile)/0.2% TFA (trifluoroacetic acid) and (b) 80% ACN/0.2% TFA as follows: 1) 0% (b), 3 rain; 2) 0–50% (b), 0.5 min; 3) 50–100% (b), 3 rain; 4) 100% (b), 2.5 rain; 5) 100–0% (b), 0.1 min; and 6) 0% (b), 5 min. At a flow rate of 1.5 ml/min, retention times of the beta-lactam nucleus and phthalic acid, as measured at 254 nm, were 2.3 and 7.2 min, respectively.

The results are shown in Table 4. Optimal range for enzyme activity occurred between pH 7.8 and 8.4.

TABLE 4

| pH | Specific Activity (μmol/min/μmol enzyme) |
| --- | --- |
| 7.0 | 125.4 |
| 7.2 | 130.4 |
| 7.4 | 155.2 |

TABLE 4-continued

| pH | Specific Activity (μmol/min/μmol enzyme) |
|---|---|
| 7.6 | 172.5 |
| 7.8 | 184.2 |
| 8.0 | 195.3 |
| 8.2 | 201.2 |
| 8.4 | 208.0 |
| 8.6 | 181.7 |
| 8.8 | 185.1 |
| 9.0 | 33.1 |

EXAMPLE 6

Optimum Reaction Temperature

Test reactions were carried out similar to Example 5 except that all incubations were performed in 50 mM potassium phosphate buffer at pH 8.2. Solutions of the substrate were pre-incubated for 5 minutes at temperatures between 2° and 60° C. The enzymatic reaction was initiated by the addition of phthalyl amidase and stopped by the addition of 1 ml methanol. Specific activity of the enzyme was determined by monitoring the hydrolysis of III by HPLC as in Example 5.

The maximum reaction rate for the enzyme was reached at 34° C. Little enzyme activity was found below 10° C. and above 50° C.

EXAMPLE 7

Optimum Salt Concentration

Test reactions were carried out similar to Example 6 except that buffer concentrations ranging from 10 to 200 mM at 32° C. were examined. All other conditions and analyses were the same.

As is apparent in Table 5, high salt concentration markedly improved the specific activity of the enzyme. The effect was of a general nature and did not appear to be dependent on specific anions or cations.

TABLE 5

| Buffer Conc. (mM) | Specific Activity (μmol/min/μmol enzyme) | | |
|---|---|---|---|
| | K Phosphate | Tris-HCl | NH4 Acetate |
| 10 | 148 | 73 | 25 |
| 50 | 300 | 230 | 50 |
| 100 | 350 | 275 | 75 |
| 200 | 360 | 300 | 100 |

EXAMPLE 8

Stability of Phthalyl Amidase

A. Effect of Ionic Strength

The stability of phthalyl amidase at pH values ranging from 6-9 was determined as described in Example 5 at 30° C. in both 20 and 200 mM potassium phosphate buffer. In 20 mM buffer, all enzyme activity was lost within 2 hours at any pH of the incubation medium. In 200 mM buffer, the enzyme retained at least 80% of its activity for 100 hours irrespective of the pH of the incubating medium. Twenty mM buffer that was supplemented with 200 mM KCl or NaCl also protected against activity loss, indicating that the enzyme stabilization was primarily dependent on the high ionic strength of the buffer.

B. Temperature Stability

The phthalyl amidase enzyme was also tested for stability at varying temperatures. The enzyme was incubated at pH 8.2 in the temperature range of 4°-50° C. for 48 hours in 50 and 200 mM phosphate buffer. In 50 mM buffer, the enzyme retained 90% of its activity for 48 hours when maintained at temperatures below 25° C., while all enzyme activity was lost within 48 hours when the incubation temperature was above 40° C. In 200 mM buffer, 80% of the enzyme activity was retained in temperatures up to 35° C. and 30% of the enzyme activity was retained after 48 hours incubation at 40° C.

EXAMPLE 9

Influence of Effectors on Enzyme Activity

The effect of various agents on the enzymatic activity of phthalyl amidase was determined using standard conditions (see Example 5). All agents were tested at 1 mM final concentration unless otherwise indicated.

It can be seen from the data in Table 6 that iodoacetate, p-HMB, and copper ions significantly reduced phthalyl amidase activity. None of the tested compounds stimulated enzyme activity significantly above that of the control.

Table 7 shows the effects of four organic solvents at three concentrations on enzyme catalysis. All four solvents tested significantly decreased enzyme activity at a concentration of 10%. Glycerol caused the least amount of inhibition of the enzyme at the highest concentration tested.

TABLE 6

| Effector Agent | % of Control Activity |
|---|---|
| Sulfhydryl agents | |
| p-HMB | 65 |
| DTNB | 98 |
| NEM | 100 |
| Iodoacetate, 1 mM | 91 |
| Iodoacetate, 10 mM | 46 |
| Metal chelators | |
| Phenanthroline | 104 |
| EDTA | 103 |
| Co-factors and reducing agents | |
| Mercaptoethanol | 105 |
| DTT | 100 |
| NAD | 101 |
| NADH | 96 |
| NADP | 99 |
| NADPH | 99 |
| ATP | 96 |
| PLP | 106 |
| THF | 100 |
| CoASH | 102 |
| THF + DTT | 100 |
| FAD | 101 |
| FAD + DTT | 100 |
| Metal Cations | |
| NaCl | 104 |
| KCl | 100 |
| CaCl$_2$ | 89 |
| CoCl$_2$ | 101 |
| CuCl$_2$ | 36 |
| FeCl$_2$ | 102 |
| FeCl$_3$ | 96 |
| MgCl$_2$ | 102 |
| MnCl$_2$ | 84 |
| NiCl$_2$ | 94 |

TABLE 6-continued

| | |
|---|---|
| ZnCl$_2$ | 100 |

DTT: dithiothreitol
p-HMB: para-hydroxy mercuric benzoate
DTNB: dithionitrobenzoate
NEM: N-ethylmaleimide
NAD: nicotinamide adenine nucleotide
NADP: nicotinamide adenine dinucleotide phosphate
NADPH: reduced form of NADP
ATP: adenosine 5'-triphosphate
PLP: pyridoxyl-5-phosphate
THF: tetrahydrofolate
FAD: flavin adenine dinucleotide

TABLE 7

| | % Residual enzyme activity | | |
|---|---|---|---|
| Solvent | 1.0% | 5.0% | 10.0% |
| Ethanol | 99 | 85 | 45 |
| DMSO | 101 | 80 | 71 |
| Glycerol | 100 | 94 | 85 |
| Methanol | 100 | 90 | 69 |

DMSO: dimethyl sulfoxide

EXAMPLE 10

Physical and Chemical Properties of Phthalyl Amidase

The molecular weight of the phthalyl amidase was determined to be 49,900 by electrospray mass spectrometry. The enzyme is monomeric with an isoelectric point estimated by isoelectric focusing to be pH 5.5. Chemical hydrolysis and amino acid analysis of the protein by standard methods are shown in Table 8. Repeated attempts to sequence the N-terminus of the purified enzyme failed, indicating that the enzyme was blocked.

TABLE 8

| Amino Acid | Number of residues in protein |
|---|---|
| Aspartate/Asparagine | 62 |
| Threonine | 21 |
| Serine | 37 |
| Glutamate/Glutamine | 52 |
| Proline | 26 |
| Glycine | 34 |
| Alanine | 50 |
| Cysteine* | 2 |
| Valine | 23 |
| Methionine | 12 |
| Isoleucine | 20 |
| Leucine | 35 |
| Tyrosine | 17 |
| Phenylalanine | 13 |
| Histidine | 11 |
| Lysine | 4 |
| Arginine | 20 |
| Tryptophan* | 13 |

*derived from nucleotide sequence of the gene

EXAMPLE 11

Substrate Specificity of Phthalyl Amidase

A. Chemical Structure Requirements for Enzyme Activity

The activity of phthalyl amidase against 25 compounds was determined. The compounds were divided into beta-lactams (Table 9), phthalyl amides (Table 10), and aromatic ring substituted amides (Table 11). Each reaction mixture (1 ml total volume) contained 2.5 μmol of compound and 0.3 units of enzyme (based on the chromogenic substrate) of the preparative scale purified enzyme, in 50 mM phosphate buffer, pH 8.0. The reactions were conducted at 30° C. Samples of the reaction mixture were taken at various times, and methanol (equal value) was added to stop the reaction. The samples were examined by HPLC to determine the extent of substrate hydrolysis. The amount of compound hydrolyzed was calculated from a standard curve of the test compound. All substrates were stable in buffer at 30° C. and pH 8.0 in the absence of enzyme for 24 hours.

As the results in Table 9 indicate, the enzyme recognizes mono- and bicyclic beta-lactam compounds containing a phthalyl group attached to the exocyclic nitrogen. However, the side chain apparently requires a 2-carboxylate group, for example, phthalate, since no hydrolysis is observed in the absence of this functional group.

A wide variety of phthalyl amides are substrates for the enzyme as shown in Table 10. Substrates include phthalylated amino acids, dipeptides, monocyclic and bicyclic beta-lactams, phenyl, benzyl, and aliphatic amines. The enzyme also exhibited esterase activity as demonstrated by its ability to hydrolyze phthalate mono methyl ester (IX). In this series, compound XIII was the most active compound found.

Using compound XIII as a standard, a variety of aromatic ring substituted compounds were examined for reactivity with the enzyme. Results are shown in Table 11. Aromatic ring substituents at the 6 position of the phthalyl ring such as F and NH$_2$ were accepted by the enzyme. A hydroxyl group at the 3 position (XXI) of the ring and a nitrogen within the aromatic ring (XX) is also acceptable. Low levels of hydrolysis occur if a tetrazole is substituted for the 2-carboxylate group (XXII). Moving the carboxylate group to the 3 (XXIV) or 4 (XXIII) position of the aromatic ring completely eliminates hydrolytic activity. Compounds lacking the 2-carboxylate (XXV–XXVIII) are not suitable substrates for the enzyme.

These results are consistent with the enzyme being a novel catalyst that removes phthalyl protecting groups from a variety of amines under mild conditions.

TABLE 9

| Compound number | Structure | Relative activity |
|---|---|---|
| I | 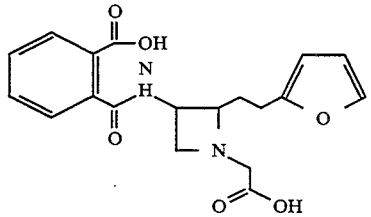 | 47.9 |
| III | 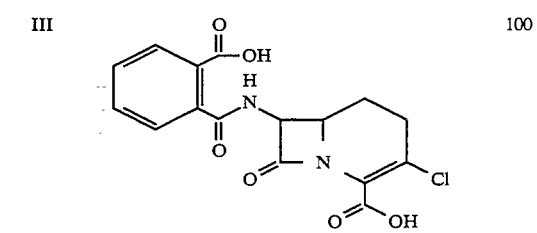 | 100 |

TABLE 9-continued

| Compound number | Structure | Relative activity |
|---|---|---|
| IV | 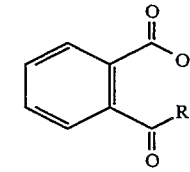 | 0 |
| V | 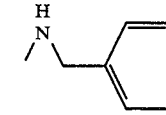 | 0 |
| VI | 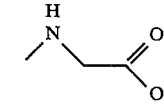 | 0 |

TABLE 10

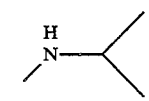

| Compound number | R Group | Relative Activity |
|---|---|---|
| II |  | 295.7 |
| III | 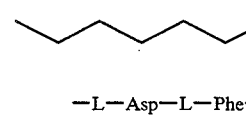 | 100.0 |
| VIII |  | 544.6 |
| IX | —OCH$_3$ | 207.6 |

TABLE 10-continued

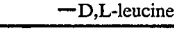

| Compound number | R Group | Relative Activity |
|---|---|---|
| X | 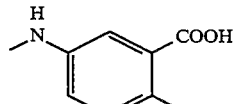 | 40.2 |
| XI | 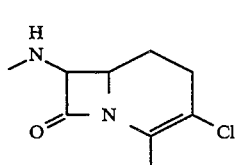 | 31.8 |
| XII | 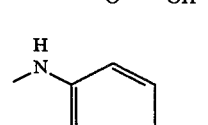 | 9.7 |
| XIII |  | 1027.2 |
| XIV | —L—Asp—L—Phe—OMe | 118.5 |
| XV | —D,L-methionine | 220.1 |
| XVI | —D,L-leucine | 90.2 |

TABLE 11

| Compound number | R Group | Relative Activity |
|---|---|---|
| XVII | 2-COOH | 100.0 |
| XVIII | 6-F, 2-COOH | 159.00 |
| XVIX | 6-NH$_2$, 2-COOH | 10.2 |
| XX | 2-COOH (with N at position 6) | 85.9 |
| XXI | 3-OH, 2-COOH | 1.3 |
| XXII | tetrazole at position 2 | 0.2 |
| XXIII | 4-COOH | 0 |
| XXIV | 3-COOH | 0 |
| XXV | 2-OH | 0 |
| XXVI | 3-OH | 0 |

TABLE 11-continued

[Structure: R-substituted benzamide linked to imidazole and hexyl-carboxylic acid chain]

| Compound number | R Group | Relative Activity |
|---|---|---|
| XXVII | 3,5-OH | 0 |
| XXVIII | 2-H | 0 |

B. Kinetic Parameters for Phthalyl Amidase

The kinetic parameters of the enzyme were determined for several representative substrates. Compounds II, XVII, and XVIII were tested using 0.9 μg/ml of enzyme. Compounds III and XI were tested using 5.14 μg/ml of enzyme. Substrate concentrations were between 0 and 25 mM and reaction time was between 2 and 20 minutes, depending on the substrate used. All reactions were run at 32° C. and at pH 8.2. The $K_m$, $V_{max}$, $K_{cat}$, and $K_{cat}/K_m$ for these substrates are shown in Table 12. $K_m$ is the Michaelis constant for enzyme kinetics, $V_{max}$ is the maximal rate of reaction calculated by the Michaelis-Menten equation, and $K_{cat}$ is the catalytic constant for an enzyme reaction.

TABLE 12

| Parameter | Substrate | | | | |
|---|---|---|---|---|---|
| | II | III[a] | XI | XVII | XVIII[b] |
| $K_m$ (mM) | 0.05 | 0.9 | 0.14 | 0.09 | 0.17 |
| $V_{max}$ (μmol/sec/μmol) | 5.95 | 7.6 | 0.27 | 1.41 | 1.94 |
| $K_{cat}$ (1/sec) | 4.95 | 6.33 | 0.22 | 1.18 | 1.61 |
| $K_{cat}/K_m$ | 99.0 | 7.0 | 1.6 | 13.1 | 9.5 |

[a] carbacepham nucleus (7-amino-3-chloro-4-carboxy-1-carba-dethioceph-3-em) (XXXIV) quantitatively monitored as the product of substrate III.
[b] for the other substrates, phthalic acid was the product monitored during the reaction.

C. Chiral and Additional Substrate Selectivity of Phthalyl Amidase.

Several additional substrates were tested in a total volume of 1 ml. Reaction mixtures contained 0.009 mg (0.6 units) of enzyme, 2.5 μmol of substrate, and buffer A. All reactions were run at 30° C. for 2 minutes except for compounds XXX and XXXII, which were run for a longer time period since they were poor substrates for the enzyme. Reactions were stopped by the addition of methanol, and phthalic acid formation was monitored by HPLC. Results are shown in Table 13.

The results show that the enzyme has a marked preference for the D isomer of N-phthalyl-phenylglycine. The L isomer was an extremely poor substrate for the enzyme. Compound XXXI had a relative activity twice that of compound III as a substrate for the enzyme. However, by substituting a sulfonate group for the carboxyl group of the phthalyl moiety, enzyme reactivity is completely lost. Again, these results show the selectivity of this enzyme for N-phthalylated amines and indicate that the enzyme has a chiral preference on the amine side of the substrate.

TABLE 13

| Compound Number | Structure | Relative Activity |
|---|---|---|
| III | [phthalamido carbacephem structure with COOH, amide, β-lactam, Cl] | 100 |
| XVIX | [D-isomer of N-phthalyl-phenylglycine] | 136 |
| XXX | [L-isomer of N-phthalyl-phenylglycine] | 1.3 |
| XXXI | [N-phthalyl-aniline with COOH] | 200 |
| XXXII | [N-(2-sulfonatobenzoyl)-aniline, SO₃K] | 0.0 |

EXAMPLE 12

Preparative Scale Synthesis of Carbacephem Nucleus

Phthalimido carbacephem (XXXIII) readily hydrolyzes to phthalamido carbacephem (III) in buffer at pH 8.0. Thus, either compound XXXIII or III can be used to prepare the carbacephem nucleus (XXXIV). Substrate (4 grams) was added to 20 ml of deionized water and the pH of the solution was adjusted to 8.0 with concentrated ammonium hydroxide. Phthalyl amidase, 80 units as determined using the chromogenic substrate (II), was added to start the reaction. Temperature was maintained at 30° C. and the pH maintained at 8.0 by adding 2 N ammonium hydroxide. After 510 minutes under these conditions, HPLC analysis of the samples from the reaction indicated that compound III was 90.0% hydrolyzed and compound XXXIII was 98% hydrolyzed. The pH of the reaction was lowered to 5.0 thereby precipitating the carbacephem nucleus. Isolated yields of the nucleus were between 65% and 77%.

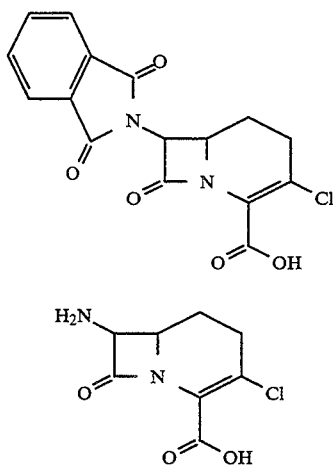

XXXIII

XXXIV

EXAMPLE 13

Expression of Met-Phthalyl Amidase in Escherichia coli

Several small scale temperature inductions of E. coli DH5α/pZPA400 were carried out to assess the amount of met-phthalyl amidase protein and enzymatic activity generated by E. coli DH5α/pZPA400. Enzymatic activity was observed by incubation of a soluble cell extract with the chromogenic substrate (II) under conditions as described in Example 3. Results are reported in Table 14.

SDS-PAGE gels of the cell extract showed a Coomassie-stained protein band corresponding to approximately 50,000 daltons that increased upon temperature induction. Partial purification of the cell extract by anion exchange chromatography yielded fractions with increased phthalyl amidase specific activity. Phthalyl amidase in these fractions catalyzed cleavage of the phthalyl group from compound III to form compound XXXIV and phthalic acid.

EXAMPLE 14

Expression of Pro-Phthalyl Amidase Open Reading Frame in Strepcomyces lividans

A 5 ml inoculum of Streptomyces lividans TK23/pZPA600 (grown for 48 hours at 30° C., 280 rpm) was added to each of two 2 L shake flasks containing 500 ml Trypticase Soy Broth medium and cultured at 30° C., 280 rpm for 24 hours. Incubations beyond 24 hours were deleterious to production of phthalyl amidase. Cells were removed by centrifugation (4° C., 15 min, 12,000×g) and phthalyl amidase activity in the cell-free broth was determined with compound III as substrate as in Example 13 (Table 14). The cell-free broth (800 ml, 0.10 mg/ml) was passed at 1 ml/min through a Mono Q column (10×10 mm (8 ml); Pharmacia). A linear gradient of 0 to 1.5 M KCl in buffer A was passed over the column and 2 ml fractions were collected. Most of the phthalyl amidase activity eluted in fractions 19 and 20 (about 0.75 M KCl).

A 1 ml aliquot of fraction 19 was concentrated 10-fold via ultrafiltration and analyzed by SDS-PAGE. A major protein band was observed at about 50,000 daltons, which corresponded to the molecular weight observed by electrospray mass spectrometry for purified mature phthalyl amidase obtained from Xanthobacter agilis. It also corresponded closely to the theoretical molecular weight predicted for a protein encoded by SEQ ID NO:1.

TABLE 14

| Expressing Organism | Plasmid | Activity in Crude Extract (nmol/min/mg) | Activity in Culture Broth (nmol/min/L) |
|---|---|---|---|
| Xanthobacter agilis | none | 63.0 | 3465 |
| Escherichia coli | pZPA400 | 0.96 | 438 |
| Streptomyces lividans | pZPA600 | 748.8 | 76,378 |

EXAMPLE 15

Use of Recombinant Phthalyl Amidase to Remove the Phthalyl Blocking Group from Phthalamido Carbacephem Activity was assayed by the addition of phthalyl amidase (30 μl of Mono Q fraction 19 from Example 14, 1.83 μg total protein) to 1.82 μg of compound III in a 1 ml reaction mixture buffered by 200 mM potassium phosphate, pH 8.2. The reaction was carried out at 32° C. for 20 minutes and stopped with the addition of 1 ml methanol. After removal of precipitate by centrifugation, an aliquot (30 μl) of the supernatant fraction was monitored by HPLC (254 nm absorbance) for both the carbacephem nucleus (XXXIV) and phthalic acid using a Zorbax C8 column (0.46×15 cm; MacMod Analytical Inc.). The reaction products were eluted by a mobile phase constructed as continuous mixed gradients from (a) 1% acetonitrile/0.2% trifluoroacetic acid and (b) 80% acetonitrile/0.2% trifluoroacetic acid. The above substrate, loracarbef nucleus, and phthalic acid eluted at 11.0, 3.4, and 5.9 minutes, respectively. HPLC peaks were identified and quantitated using data generated by known amounts of authentic compounds. The specific activity of recombinant phthalyl amidase derived from fraction 19 for conversion of substrate was 9.5 μmol/min/mg protein.

EXAMPLE 16

Use of Recombinant Phthalyl Amidase to Remove the Phthalyl Blocking Group from Phthalimido-Aspartame In the synthesis of aspartame, the bivalent protection of the amino group of L-aspartic acid via a phthalimido moiety gives a superior substrate for a lyase-catalyzed condensation with L-phenylalanine methyl ester. However, an efficient method to convert the phthalimido-protected compound back to the amine was previously lacking. Following the condensation reaction, mild base was used to open the phthalimido moiety to a phthalamido moiety and recombinant phthalyl amidase was then used to catalyze hydrolysis of the latter to aspartame and phthalic acid (see Table 10).

We claim:

1. An isolated phthalyl amidase enzyme that has the following properties:

a) Reactivity: said enzyme catalyzes the removal of the phthalyl group from phthalyl amides generating phthalate and an amine;
b) Substrate specificity: said enzyme hydrolyzes phthalylated amino acids, peptides, beta-lactams, aromatic and aliphatic amines; substitutions allowed on the phthalyl group include 6—F, 6—NH$_2$, 3—OH, and a nitrogen in the aromatic ring ortho to the carboxyl group attached to the amine;
c) Reactive pH range: 5.5 to 9.0, with optimum pH of 8.0±0.4;
d) Reactive temperature range: 10° to 50° C., with optimum temperature of 30° C.±4° C. at pH 8.0;
e) Temperature stability: At 200 mM buffer, 80% of enzyme activity retained at 35° C. for 48 hours;
f) Influence of effectors: Iodoacetate, p-HMB, and Cu$^{++}$ exert inhibitory activity;
g) Molecular weight: approximately 49,900 daltons;
h) Subunits: one;
i) K$_m$: 0.9 mM in 50 mM potassium phosphate buffer, 30° C., pH 8.0, when phthalamido carbacephem is the substrate.

2. The isolated phthalyl amidase of claim 1 produced by aerobically cultivating Xanthobacter agilis, or phthalyl amidase-producing mutants thereof which retain the identifying characteristics of the parent strain, in an aqueous nutrient medium containing a source for carbon and nitrogen and mineral salts at an initial pH between 6° and 8° at 25° to 30° C., digesting the cells, and purifying the phthalyl amidase.

3. The isolated phthalyl amidase of claim 2 wherein the cultured organism is Xanthobacter agilis NRRL B-21115, or phthalyl amidase-producing mutants thereof which retain the identifying characteristics of the parent strain.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
  ( A ) LENGTH: 1359 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 1..1356

( x i ) SEQUENCE DESCRIPTION: SEQ ID NO:1:

```
CAG GCG CCG TCT GTG CAC CAA CAC GTC GCC TTC ACT GAG GAA ATT GGA      48
Gln Ala Pro Ser Val His Gln His Val Ala Phe Thr Glu Glu Ile Gly
 1               5                  10                  15

GAC CTT CCC GAC GGC TCA AGT TAC ATG ATC CGT GTG CCG GAG AAC TGG      96
Asp Leu Pro Asp Gly Ser Ser Tyr Met Ile Arg Val Pro Glu Asn Trp
             20                  25                  30

AAC GGC GTG TTA ATT CGC GAC CTA GAC CTT GTC AGC GGC ACC AGC AAT     144
Asn Gly Val Leu Ile Arg Asp Leu Asp Leu Val Ser Gly Thr Ser Asn
         35                  40                  45

TCT AAC GCC GCA AGG TAC GAA ACC ATG CTG AAA GAA GGT TTT GCC GTT     192
Ser Asn Ala Ala Arg Tyr Glu Thr Met Leu Lys Glu Gly Phe Ala Val
 50                  55                  60

GCT GGC ACG GCG AGG CAT CCC CTT CGG CAA TGG CAA TAT GAC CCC GCT     240
Ala Gly Thr Ala Arg His Pro Leu Arg Gln Trp Gln Tyr Asp Pro Ala
 65                  70                  75                  80

CAC GAG ATT GAA AAC CTC AAT CAC GTG CTG GAC ACA TTC GAG GAA AAT     288
His Glu Ile Glu Asn Leu Asn His Val Leu Asp Thr Phe Glu Glu Asn
                 85                  90                  95

TAC GGT TCA CCT GAA AGA GTT ATC CAG TAC GGT TGC TCG GGT GGG GCA     336
Tyr Gly Ser Pro Glu Arg Val Ile Gln Tyr Gly Cys Ser Gly Gly Ala
            100                 105                 110

CAC GTG TCA CTA GCC GTG GCA GAG GAC TTC TCG GAC CGC GTA GAT GGC     384
His Val Ser Leu Ala Val Ala Glu Asp Phe Ser Asp Arg Val Asp Gly
        115                 120                 125

TCA GTT GCT CTA GCT GCT CAT ACT CCT GTC TGG ATA ATG AAT TCT TTC     432
Ser Val Ala Leu Ala Ala His Thr Pro Val Trp Ile Met Asn Ser Phe
130                 135                 140
```

| | | | | | | | | | | | | | | | | |
|---|---|---|---|---|---|---|---|---|---|---|---|---|---|---|---|---|
| TTG | GAC | GGA | TGG | TTT | TCG | CTG | CAG | TCT | CTG | ATC | GGC | GAG | TAC | TAT | GTA | 480 |
| Leu | Asp | Gly | Trp | Phe | Ser | Leu | Gln | Ser | Leu | Ile | Gly | Glu | Tyr | Tyr | Val | |
| 145 | | | | 150 | | | | | 155 | | | | | | 160 | |
| GAA | GCT | GGT | CAC | GGC | CCA | CTT | TCG | GAT | CTC | GCT | ATT | ACG | AAA | CTG | CCC | 528 |
| Glu | Ala | Gly | His | Gly | Pro | Leu | Ser | Asp | Leu | Ala | Ile | Thr | Lys | Leu | Pro | |
| | | | | 165 | | | | 170 | | | | | 175 | | | |
| AAT | GAT | GGT | AGC | TCT | AAT | TCG | AGC | GGT | CAT | GGA | ATG | GAA | GGA | GAT | CTT | 576 |
| Asn | Asp | Gly | Ser | Ser | Asn | Ser | Ser | Gly | His | Gly | Met | Glu | Gly | Asp | Leu | |
| | | | 180 | | | | | 185 | | | | | 190 | | | |
| CCT | GCC | GCG | TGG | CGC | AAC | GCG | TTC | ACC | GCT | GCT | AAC | GCC | ACA | CCT | GAG | 624 |
| Pro | Ala | Ala | Trp | Arg | Asn | Ala | Phe | Thr | Ala | Ala | Asn | Ala | Thr | Pro | Glu | |
| | | 195 | | | | | 200 | | | | | 205 | | | | |
| GGT | CGC | GCA | CGC | ATG | GCA | CTA | GCC | TTT | GCG | CTC | GGT | CAG | TGG | TCT | CCG | 672 |
| Gly | Arg | Ala | Arg | Met | Ala | Leu | Ala | Phe | Ala | Leu | Gly | Gln | Trp | Ser | Pro | |
| | | 210 | | | | | 215 | | | | | 220 | | | | |
| TGG | TTG | GCC | GAC | AAC | ACG | CCC | CAA | CCT | GAT | CTC | GAT | GAT | CCT | GAG | GCC | 720 |
| Trp | Leu | Ala | Asp | Asn | Thr | Pro | Gln | Pro | Asp | Leu | Asp | Asp | Pro | Glu | Ala | |
| 225 | | | | | 230 | | | | | 235 | | | | | 240 | |
| ATC | GCG | GAT | TCC | GTA | TAT | GAG | TCT | GCC | ATG | CGA | CTT | GCA | GGA | AGC | CCT | 768 |
| Ile | Ala | Asp | Ser | Val | Tyr | Glu | Ser | Ala | Met | Arg | Leu | Ala | Gly | Ser | Pro | |
| | | | | 245 | | | | | 250 | | | | | 255 | | |
| GGG | GGA | GAA | GCG | CGC | ATA | ATG | TTC | GAG | AAC | GCC | GCT | CGA | GGG | CAA | CAG | 816 |
| Gly | Gly | Glu | Ala | Arg | Ile | Met | Phe | Glu | Asn | Ala | Ala | Arg | Gly | Gln | Gln | |
| | | | 260 | | | | | 265 | | | | | 270 | | | |
| CTC | TCT | TGG | AAC | GAC | GAC | ATC | GAC | TAT | GCG | GAT | TTC | TGG | GAG | AAC | TCA | 864 |
| Leu | Ser | Trp | Asn | Asp | Asp | Ile | Asp | Tyr | Ala | Asp | Phe | Trp | Glu | Asn | Ser | |
| | | 275 | | | | | 280 | | | | | 285 | | | | |
| AAC | CCA | GCC | ATG | AAG | AGC | GCC | GTT | CAG | GAG | CTG | TAC | GAC | ACG | GCC | GGC | 912 |
| Asn | Pro | Ala | Met | Lys | Ser | Ala | Val | Gln | Glu | Leu | Tyr | Asp | Thr | Ala | Gly | |
| | 290 | | | | | 295 | | | | | 300 | | | | | |
| CTT | GAT | CTG | CAG | TCC | GAT | ATA | GAA | ACG | GTA | AAT | TCC | CAG | CCA | CGC | ATA | 960 |
| Leu | Asp | Leu | Gln | Ser | Asp | Ile | Glu | Thr | Val | Asn | Ser | Gln | Pro | Arg | Ile | |
| 305 | | | | 310 | | | | | 315 | | | | | | 320 | |
| GAG | GCA | TCG | CAG | TAT | GCG | CTC | GAC | TAC | TGG | AAC | ACG | CCA | GGT | CGC | AAT | 1008 |
| Glu | Ala | Ser | Gln | Tyr | Ala | Leu | Asp | Tyr | Trp | Asn | Thr | Pro | Gly | Arg | Asn | |
| | | | | 325 | | | | | 330 | | | | | 335 | | |
| GTC | ATT | GGC | GAC | CCC | GAA | GTT | CCT | GTG | CTG | CGC | CTG | CAT | ATG | ATA | GGC | 1056 |
| Val | Ile | Gly | Asp | Pro | Glu | Val | Pro | Val | Leu | Arg | Leu | His | Met | Ile | Gly | |
| | | | 340 | | | | | 345 | | | | | 350 | | | |
| GAC | TAC | CAA | ATT | CCC | TAT | AGT | CTT | GTA | CAG | GGC | TAC | AGC | GAT | CTT | ATC | 1104 |
| Asp | Tyr | Gln | Ile | Pro | Tyr | Ser | Leu | Val | Gln | Gly | Tyr | Ser | Asp | Leu | Ile | |
| | | 355 | | | | | 360 | | | | | 365 | | | | |
| TCA | GAG | AAC | AAC | AAT | GAT | GAC | TTG | TAC | AGA | ACT | GCT | TTT | GTG | CAA | TCC | 1152 |
| Ser | Glu | Asn | Asn | Asn | Asp | Asp | Leu | Tyr | Arg | Thr | Ala | Phe | Val | Gln | Ser | |
| | 370 | | | | | 375 | | | | | 380 | | | | | |
| ACT | GGA | CAC | TGC | AAT | TTC | ACA | GCT | GCA | GAA | AGT | TCC | GCT | GCG | ATT | GAG | 1200 |
| Thr | Gly | His | Cys | Asn | Phe | Thr | Ala | Ala | Glu | Ser | Ser | Ala | Ala | Ile | Glu | |
| 385 | | | | 390 | | | | | 395 | | | | | | 400 | |
| GTC | ATG | ATG | CAA | CGG | CTT | GAC | ACG | GGT | GAG | TGG | CCG | AGC | ACC | GAG | CCG | 1248 |
| Val | Met | Met | Gln | Arg | Leu | Asp | Thr | Gly | Glu | Trp | Pro | Ser | Thr | Glu | Pro | |
| | | | | 405 | | | | | 410 | | | | | 415 | | |
| GAT | GAT | CTG | AAT | GCA | ATT | GCC | GAA | GCC | TCA | AAC | ACC | GGA | ACT | GAA | GCA | 1296 |
| Asp | Asp | Leu | Asn | Ala | Ile | Ala | Glu | Ala | Ser | Asn | Thr | Gly | Thr | Glu | Ala | |
| | | | 420 | | | | | 425 | | | | | 430 | | | |
| CGT | TTC | ATG | GCC | CTA | GAT | GGC | TGG | GAA | ATA | CCC | GAG | TAC | AAT | CGT | ACT | 1344 |
| Arg | Phe | Met | Ala | Leu | Asp | Gly | Trp | Glu | Ile | Pro | Glu | Tyr | Asn | Arg | Thr | |
| | | 435 | | | | | 440 | | | | | 445 | | | | |
| TGG | AAG | CCT | GAA | TAA | | | | | | | | | | | | 1359 |
| Trp | Lys | Pro | Glu | | | | | | | | | | | | | |
| | 450 | | | | | | | | | | | | | | | |

( 2 ) INFORMATION FOR SEQ ID NO:2:

( i ) SEQUENCE CHARACTERISTICS:
   ( A ) LENGTH: 452 amino acids
   ( B ) TYPE: amino acid
   ( D ) TOPOLOGY: linear ( i i ) MOLECULE TYPE: protein ( x i ) SEQUENCE DESCRIPTION: SEQ ID NO:2:

| Gln | Ala | Pro | Ser | Val | His | Gln | His | Val | Ala | Phe | Thr | Glu | Glu | Ile | Gly |
|---|---|---|---|---|---|---|---|---|---|---|---|---|---|---|---|
| 1 | | | | 5 | | | | | 10 | | | | | 15 | |
| Asp | Leu | Pro | Asp | Gly | Ser | Ser | Tyr | Met | Ile | Arg | Val | Pro | Glu | Asn | Trp |
| | | | 20 | | | | | 25 | | | | | 30 | | |
| Asn | Gly | Val | Leu | Ile | Arg | Asp | Leu | Asp | Leu | Val | Ser | Gly | Thr | Ser | Asn |
| | | | 35 | | | | 40 | | | | | 45 | | | |
| Ser | Asn | Ala | Ala | Arg | Tyr | Glu | Thr | Met | Leu | Lys | Glu | Gly | Phe | Ala | Val |
| | 50 | | | | | 55 | | | | | 60 | | | | |
| Ala | Gly | Thr | Ala | Arg | His | Pro | Leu | Arg | Gln | Trp | Gln | Tyr | Asp | Pro | Ala |
| 65 | | | | | 70 | | | | 75 | | | | | | 80 |
| His | Glu | Ile | Glu | Asn | Leu | Asn | His | Val | Leu | Asp | Thr | Phe | Glu | Glu | Asn |
| | | | | 85 | | | | | 90 | | | | | 95 | |
| Tyr | Gly | Ser | Pro | Glu | Arg | Val | Ile | Gln | Tyr | Gly | Cys | Ser | Gly | Gly | Ala |
| | | | 100 | | | | | 105 | | | | | 110 | | |
| His | Val | Ser | Leu | Ala | Val | Ala | Glu | Asp | Phe | Ser | Asp | Arg | Val | Asp | Gly |
| | | | 115 | | | | | 120 | | | | | 125 | | |
| Ser | Val | Ala | Leu | Ala | Ala | His | Thr | Pro | Val | Trp | Ile | Met | Asn | Ser | Phe |
| | 130 | | | | | 135 | | | | | 140 | | | | |
| Leu | Asp | Gly | Trp | Phe | Ser | Leu | Gln | Ser | Leu | Ile | Gly | Glu | Tyr | Tyr | Val |
| 145 | | | | | 150 | | | | | 155 | | | | | 160 |
| Glu | Ala | Gly | His | Gly | Pro | Leu | Ser | Asp | Leu | Ala | Ile | Thr | Lys | Leu | Pro |
| | | | | 165 | | | | | 170 | | | | | 175 | |
| Asn | Asp | Gly | Ser | Ser | Asn | Ser | Ser | Gly | His | Gly | Met | Glu | Gly | Asp | Leu |
| | | | 180 | | | | | 185 | | | | | 190 | | |
| Pro | Ala | Ala | Trp | Arg | Asn | Ala | Phe | Thr | Ala | Ala | Asn | Ala | Thr | Pro | Glu |
| | | 195 | | | | | 200 | | | | | 205 | | | |
| Gly | Arg | Ala | Arg | Met | Ala | Leu | Ala | Phe | Ala | Leu | Gly | Gln | Trp | Ser | Pro |
| | 210 | | | | | 215 | | | | | 220 | | | | |
| Trp | Leu | Ala | Asp | Asn | Thr | Pro | Gln | Pro | Asp | Leu | Asp | Asp | Pro | Glu | Ala |
| 225 | | | | | 230 | | | | | 235 | | | | | 240 |
| Ile | Ala | Asp | Ser | Val | Tyr | Glu | Ser | Ala | Met | Arg | Leu | Ala | Gly | Ser | Pro |
| | | | | 245 | | | | | 250 | | | | | 255 | |
| Gly | Gly | Glu | Ala | Arg | Ile | Met | Phe | Glu | Asn | Ala | Ala | Arg | Gly | Gln | Gln |
| | | | 260 | | | | | 265 | | | | | 270 | | |
| Leu | Ser | Trp | Asn | Asp | Asp | Ile | Asp | Tyr | Ala | Asp | Phe | Trp | Glu | Asn | Ser |
| | | 275 | | | | | 280 | | | | | 285 | | | |
| Asn | Pro | Ala | Met | Lys | Ser | Ala | Val | Gln | Glu | Leu | Tyr | Asp | Thr | Ala | Gly |
| | 290 | | | | | 295 | | | | | 300 | | | | |
| Leu | Asp | Leu | Gln | Ser | Asp | Ile | Glu | Thr | Val | Asn | Ser | Gln | Pro | Arg | Ile |
| 305 | | | | | 310 | | | | | 315 | | | | | 320 |
| Glu | Ala | Ser | Gln | Tyr | Ala | Leu | Asp | Tyr | Trp | Asn | Thr | Pro | Gly | Arg | Asn |
| | | | | 325 | | | | | 330 | | | | | 335 | |
| Val | Ile | Gly | Asp | Pro | Glu | Val | Pro | Val | Leu | Arg | Leu | His | Met | Ile | Gly |
| | | | 340 | | | | | 345 | | | | | 350 | | |
| Asp | Tyr | Gln | Ile | Pro | Tyr | Ser | Leu | Val | Gln | Gly | Tyr | Ser | Asp | Leu | Ile |
| | | | 355 | | | | | 360 | | | | | 365 | | |
| Ser | Glu | Asn | Asn | Asn | Asp | Asp | Leu | Tyr | Arg | Thr | Ala | Phe | Val | Gln | Ser |
| | 370 | | | | | 375 | | | | | 380 | | | | |

```
Thr  Gly  His  Cys  Asn  Phe  Thr  Ala  Ala  Glu  Ser  Ser  Ala  Ala  Ile  Glu
385                 390                      395                           400

Val  Met  Met  Gln  Arg  Leu  Asp  Thr  Gly  Glu  Trp  Pro  Ser  Thr  Glu  Pro
                    405                      410                 415

Asp  Asp  Leu  Asn  Ala  Ile  Ala  Glu  Ala  Ser  Asn  Thr  Gly  Thr  Glu  Ala
                    420                      425                      430

Arg  Phe  Met  Ala  Leu  Asp  Gly  Trp  Glu  Ile  Pro  Glu  Tyr  Asn  Arg  Thr
               435                 440                      445

Trp  Lys  Pro  Glu
               450
```

( 2 ) INFORMATION FOR SEQ ID NO:3:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1482

( x i ) SEQUENCE DESCRIPTION: SEQ ID NO:3:

```
ATG  ATA  ATC  AAG  GGT  AGT  GTA  CCG  GGT  AAA  GCC  GGA  GGA  AAA  CCT  CGA     48
Met  Ile  Ile  Lys  Gly  Ser  Val  Pro  Gly  Lys  Ala  Gly  Gly  Lys  Pro  Arg
1                   5                        10                       15

GCG  ACC  ATC  TTT  CAT  AGT  TCT  ATT  GCA  ACG  CTA  CTT  TTA  ACC  ACA  GTC     96
Ala  Thr  Ile  Phe  His  Ser  Ser  Ile  Ala  Thr  Leu  Leu  Leu  Thr  Thr  Val
                    20                       25                       30

TCA  CTG  TCA  GGA  GTA  GCG  CCA  GCA  TTT  GCA  CAG  GCG  CCG  TCT  GTG  CAC    144
Ser  Leu  Ser  Gly  Val  Ala  Pro  Ala  Phe  Ala  Gln  Ala  Pro  Ser  Val  His
               35                       40                       45

CAA  CAC  GTC  GCC  TTC  ACT  GAG  GAA  ATT  GGA  GAC  CTT  CCC  GAC  GGC  TCA    192
Gln  His  Val  Ala  Phe  Thr  Glu  Glu  Ile  Gly  Asp  Leu  Pro  Asp  Gly  Ser
          50                       55                       60

AGT  TAC  ATG  ATC  CGT  GTG  CCG  GAG  AAC  TGG  AAC  GGC  GTG  TTA  ATT  CGC    240
Ser  Tyr  Met  Ile  Arg  Val  Pro  Glu  Asn  Trp  Asn  Gly  Val  Leu  Ile  Arg
65                       70                       75                       80

GAC  CTA  GAC  CTT  GTC  AGC  GGC  ACC  AGC  AAT  TCT  AAC  GCC  GCA  AGG  TAC    288
Asp  Leu  Asp  Leu  Val  Ser  Gly  Thr  Ser  Asn  Ser  Asn  Ala  Ala  Arg  Tyr
                    85                       90                       95

GAA  ACC  ATG  CTG  AAA  GAA  GGT  TTT  GCC  GTT  GCT  GGC  ACG  GCG  AGG  CAT    336
Glu  Thr  Met  Leu  Lys  Glu  Gly  Phe  Ala  Val  Ala  Gly  Thr  Ala  Arg  His
               100                      105                      110

CCC  CTT  CGG  CAA  TGG  CAA  TAT  GAC  CCC  GCT  CAC  GAG  ATT  GAA  AAC  CTC    384
Pro  Leu  Arg  Gln  Trp  Gln  Tyr  Asp  Pro  Ala  His  Glu  Ile  Glu  Asn  Leu
          115                      120                      125

AAT  CAC  GTG  CTG  GAC  ACA  TTC  GAG  GAA  AAT  TAC  GGT  TCA  CCT  GAA  AGA    432
Asn  His  Val  Leu  Asp  Thr  Phe  Glu  Glu  Asn  Tyr  Gly  Ser  Pro  Glu  Arg
     130                      135                      140

GTT  ATC  CAG  TAC  GGT  TGC  TCG  GGT  GGG  GCA  CAC  GTG  TCA  CTA  GCC  GTG    480
Val  Ile  Gln  Tyr  Gly  Cys  Ser  Gly  Gly  Ala  His  Val  Ser  Leu  Ala  Val
145                      150                      155                      160

GCA  GAG  GAC  TTC  TCG  GAC  CGC  GTA  GAT  GGC  TCA  GTT  GCT  CTA  GCT  GCT    528
Ala  Glu  Asp  Phe  Ser  Asp  Arg  Val  Asp  Gly  Ser  Val  Ala  Leu  Ala  Ala
                    165                      170                      175

CAT  ACT  CCT  GTC  TGG  ATA  ATG  AAT  TCT  TTC  TTG  GAC  GGA  TGG  TTT  TCG    576
His  Thr  Pro  Val  Trp  Ile  Met  Asn  Ser  Phe  Leu  Asp  Gly  Trp  Phe  Ser
               180                      185                      190

CTG  CAG  TCT  CTG  ATC  GGC  GAG  TAC  TAT  GTA  GAA  GCT  GGT  CAC  GGC  CCA    624
Leu  Gln  Ser  Leu  Ile  Gly  Glu  Tyr  Tyr  Val  Glu  Ala  Gly  His  Gly  Pro
```

-continued

```
              195                         200                        205
CTT  TCG  GAT  CTC  GCT  ATT  ACG  AAA  CTG  CCC  AAT  GAT  GGT  AGC  TCT  AAT      672
Leu  Ser  Asp  Leu  Ala  Ile  Thr  Lys  Leu  Pro  Asn  Asp  Gly  Ser  Ser  Asn
     210                      215                      220

TCG  AGC  GGT  CAT  GGA  ATG  GAA  GGA  GAT  CTT  CCT  GCC  GCG  TGG  CGC  AAC      720
Ser  Ser  Gly  His  Gly  Met  Glu  Gly  Asp  Leu  Pro  Ala  Ala  Trp  Arg  Asn
225                           230                      235                     240

GCG  TTC  ACC  GCT  GCT  AAC  GCC  ACA  CCT  GAG  GGT  CGC  GCA  CGC  ATG  GCA      768
Ala  Phe  Thr  Ala  Ala  Asn  Ala  Thr  Pro  Glu  Gly  Arg  Ala  Arg  Met  Ala
                    245                           250                      255

CTA  GCC  TTT  GCG  CTC  GGT  CAG  TGG  TCT  CCG  TGG  TTG  GCC  GAC  AAC  ACG      816
Leu  Ala  Phe  Ala  Leu  Gly  Gln  Trp  Ser  Pro  Trp  Leu  Ala  Asp  Asn  Thr
               260                      265                      270

CCC  CAA  CCT  GAT  CTC  GAT  GAT  CCT  GAG  GCC  ATC  GCG  GAT  TCC  GTA  TAT      864
Pro  Gln  Pro  Asp  Leu  Asp  Asp  Pro  Glu  Ala  Ile  Ala  Asp  Ser  Val  Tyr
          275                           280                      285

GAG  TCT  GCC  ATG  CGA  CTT  GCA  GGA  AGC  CCT  GGG  GGA  GAA  GCG  CGC  ATA      912
Glu  Ser  Ala  Met  Arg  Leu  Ala  Gly  Ser  Pro  Gly  Gly  Glu  Ala  Arg  Ile
     290                           295                      300

ATG  TTC  GAG  AAC  GCC  GCT  CGA  GGG  CAA  CAG  CTC  TCT  TGG  AAC  GAC  GAC      960
Met  Phe  Glu  Asn  Ala  Ala  Arg  Gly  Gln  Gln  Leu  Ser  Trp  Asn  Asp  Asp
305                           310                      315                     320

ATC  GAC  TAT  GCG  GAT  TTC  TGG  GAG  AAC  TCA  AAC  CCA  GCC  ATG  AAG  AGC     1008
Ile  Asp  Tyr  Ala  Asp  Phe  Trp  Glu  Asn  Ser  Asn  Pro  Ala  Met  Lys  Ser
                    325                           330                      335

GCC  GTT  CAG  GAG  CTG  TAC  GAC  ACG  GCC  GGC  CTT  GAT  CTG  CAG  TCC  GAT     1056
Ala  Val  Gln  Glu  Leu  Tyr  Asp  Thr  Ala  Gly  Leu  Asp  Leu  Gln  Ser  Asp
               340                      345                      350

ATA  GAA  ACG  GTA  AAT  TCC  CAG  CCA  CGC  ATA  GAG  GCA  TCG  CAG  TAT  GCG     1104
Ile  Glu  Thr  Val  Asn  Ser  Gln  Pro  Arg  Ile  Glu  Ala  Ser  Gln  Tyr  Ala
          355                           360                      365

CTC  GAC  TAC  TGG  AAC  ACG  CCA  GGT  CGC  AAT  GTC  ATT  GGC  GAC  CCC  GAA     1152
Leu  Asp  Tyr  Trp  Asn  Thr  Pro  Gly  Arg  Asn  Val  Ile  Gly  Asp  Pro  Glu
     370                           375                      380

GTT  CCT  GTG  CTG  CGC  CTG  CAT  ATG  ATA  GGC  GAC  TAC  CAA  ATT  CCC  TAT     1200
Val  Pro  Val  Leu  Arg  Leu  His  Met  Ile  Gly  Asp  Tyr  Gln  Ile  Pro  Tyr
385                           390                      395                     400

AGT  CTT  GTA  CAG  GGC  TAC  AGC  GAT  CTT  ATC  TCA  GAG  AAC  AAC  AAT  GAT     1248
Ser  Leu  Val  Gln  Gly  Tyr  Ser  Asp  Leu  Ile  Ser  Glu  Asn  Asn  Asn  Asp
                    405                           410                      415

GAC  TTG  TAC  AGA  ACT  GCT  TTT  GTG  CAA  TCC  ACT  GGA  CAC  TGC  AAT  TTC     1296
Asp  Leu  Tyr  Arg  Thr  Ala  Phe  Val  Gln  Ser  Thr  Gly  His  Cys  Asn  Phe
               420                      425                      430

ACA  GCT  GCA  GAA  AGT  TCC  GCT  GCG  ATT  GAG  GTC  ATG  ATG  CAA  CGG  CTT     1344
Thr  Ala  Ala  Glu  Ser  Ser  Ala  Ala  Ile  Glu  Val  Met  Met  Gln  Arg  Leu
          435                           440                      445

GAC  ACG  GGT  GAG  TGG  CCG  AGC  ACC  GAG  CCG  GAT  GAT  CTG  AAT  GCA  ATT     1392
Asp  Thr  Gly  Glu  Trp  Pro  Ser  Thr  Glu  Pro  Asp  Asp  Leu  Asn  Ala  Ile
     450                           455                      460

GCC  GAA  GCC  TCA  AAC  ACC  GGA  ACT  GAA  GCA  CGT  TTC  ATG  GCC  CTA  GAT     1440
Ala  Glu  Ala  Ser  Asn  Thr  Gly  Thr  Glu  Ala  Arg  Phe  Met  Ala  Leu  Asp
465                           470                      475                     480

GGC  TGG  GAA  ATA  CCC  GAG  TAC  AAT  CGT  ACT  TGG  AAG  CCT  GAA  TAA          1485
Gly  Trp  Glu  Ile  Pro  Glu  Tyr  Asn  Arg  Thr  Trp  Lys  Pro  Glu
               485                           490
```

( 2 ) INFORMATION FOR SEQ ID NO:4:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ile | Ile | Lys | Gly | Ser | Val | Pro | Gly | Lys | Ala | Gly | Gly | Lys | Pro | Arg |
|---|---|---|---|---|---|---|---|---|---|---|---|---|---|---|---|
| 1 | | | | 5 | | | | | 10 | | | | | 15 | |
| Ala | Thr | Ile | Phe | His | Ser | Ser | Ile | Ala | Thr | Leu | Leu | Leu | Thr | Thr | Val |
| | | | 20 | | | | 25 | | | | | 30 | | | |
| Ser | Leu | Ser | Gly | Val | Ala | Pro | Ala | Phe | Ala | Gln | Ala | Pro | Ser | Val | His |
| | | 35 | | | | | 40 | | | | | 45 | | | |
| Gln | His | Val | Ala | Phe | Thr | Glu | Glu | Ile | Gly | Asp | Leu | Pro | Asp | Gly | Ser |
| | 50 | | | | | 55 | | | | | 60 | | | | |
| Ser | Tyr | Met | Ile | Arg | Val | Pro | Glu | Asn | Trp | Asn | Gly | Val | Leu | Ile | Arg |
| 65 | | | | | 70 | | | | | 75 | | | | | 80 |
| Asp | Leu | Asp | Leu | Val | Ser | Gly | Thr | Ser | Asn | Ser | Asn | Ala | Ala | Arg | Tyr |
| | | | | 85 | | | | | 90 | | | | | 95 | |
| Glu | Thr | Met | Leu | Lys | Glu | Gly | Phe | Ala | Val | Ala | Gly | Thr | Ala | Arg | His |
| | | | 100 | | | | | 105 | | | | | 110 | | |
| Pro | Leu | Arg | Gln | Trp | Gln | Tyr | Asp | Pro | Ala | His | Glu | Ile | Glu | Asn | Leu |
| | | 115 | | | | | 120 | | | | | 125 | | | |
| Asn | His | Val | Leu | Asp | Thr | Phe | Glu | Glu | Asn | Tyr | Gly | Ser | Pro | Glu | Arg |
| | 130 | | | | | 135 | | | | | 140 | | | | |
| Val | Ile | Gln | Tyr | Gly | Cys | Ser | Gly | Gly | Ala | His | Val | Ser | Leu | Ala | Val |
| 145 | | | | | 150 | | | | | 155 | | | | | 160 |
| Ala | Glu | Asp | Phe | Ser | Asp | Arg | Val | Asp | Gly | Ser | Val | Ala | Leu | Ala | Ala |
| | | | | 165 | | | | | 170 | | | | | 175 | |
| His | Thr | Pro | Val | Trp | Ile | Met | Asn | Ser | Phe | Leu | Asp | Gly | Trp | Phe | Ser |
| | | | 180 | | | | | 185 | | | | | 190 | | |
| Leu | Gln | Ser | Leu | Ile | Gly | Glu | Tyr | Tyr | Val | Glu | Ala | Gly | His | Gly | Pro |
| | | 195 | | | | | 200 | | | | | 205 | | | |
| Leu | Ser | Asp | Leu | Ala | Ile | Thr | Lys | Leu | Pro | Asn | Asp | Gly | Ser | Ser | Asn |
| | 210 | | | | | 215 | | | | | 220 | | | | |
| Ser | Ser | Gly | His | Gly | Met | Glu | Gly | Asp | Leu | Pro | Ala | Ala | Trp | Arg | Asn |
| 225 | | | | | 230 | | | | | 235 | | | | | 240 |
| Ala | Phe | Thr | Ala | Ala | Asn | Ala | Thr | Pro | Glu | Gly | Arg | Ala | Arg | Met | Ala |
| | | | | 245 | | | | | 250 | | | | | 255 | |
| Leu | Ala | Phe | Ala | Leu | Gly | Gln | Trp | Ser | Pro | Trp | Leu | Ala | Asp | Asn | Thr |
| | | | 260 | | | | | 265 | | | | | 270 | | |
| Pro | Gln | Pro | Asp | Leu | Asp | Asp | Pro | Glu | Ala | Ile | Ala | Asp | Ser | Val | Tyr |
| | | 275 | | | | | 280 | | | | | 285 | | | |
| Glu | Ser | Ala | Met | Arg | Leu | Ala | Gly | Ser | Pro | Gly | Gly | Glu | Ala | Arg | Ile |
| | 290 | | | | | 295 | | | | | 300 | | | | |
| Met | Phe | Glu | Asn | Ala | Ala | Arg | Gly | Gln | Gln | Leu | Ser | Trp | Asn | Asp | Asp |
| 305 | | | | | 310 | | | | | 315 | | | | | 320 |
| Ile | Asp | Tyr | Ala | Asp | Phe | Trp | Glu | Asn | Ser | Asn | Pro | Ala | Met | Lys | Ser |
| | | | | 325 | | | | | 330 | | | | | 335 | |
| Ala | Val | Gln | Glu | Leu | Tyr | Asp | Thr | Ala | Gly | Leu | Asp | Leu | Gln | Ser | Asp |
| | | | 340 | | | | | 345 | | | | | 350 | | |
| Ile | Glu | Thr | Val | Asn | Ser | Gln | Pro | Arg | Ile | Glu | Ala | Ser | Gln | Tyr | Ala |
| | | 355 | | | | | 360 | | | | | 365 | | | |
| Leu | Asp | Tyr | Trp | Asn | Thr | Pro | Gly | Arg | Asn | Val | Ile | Gly | Asp | Pro | Glu |
| | 370 | | | | | 375 | | | | | 380 | | | | |
| Val | Pro | Val | Leu | Arg | Leu | His | Met | Ile | Gly | Asp | Tyr | Gln | Ile | Pro | Tyr |
| 385 | | | | | 390 | | | | | 395 | | | | | 400 |
| Ser | Leu | Val | Gln | Gly | Tyr | Ser | Asp | Leu | Ile | Ser | Glu | Asn | Asn | Asn | Asp |
| | | | | 405 | | | | | 410 | | | | | 415 | |

|    |    |    |    |    |    |    |    |    |    |    |    |    |    |
|----|----|----|----|----|----|----|----|----|----|----|----|----|----|
| Asp | Leu | Tyr | Arg<br>420 | Thr | Ala | Phe | Val | Gln<br>425 | Ser | Thr | Gly | His | Cys<br>430 | Asn | Phe |
| Thr | Ala | Ala<br>435 | Glu | Ser | Ser | Ala | Ala<br>440 | Ile | Glu | Val | Met | Met<br>445 | Gln | Arg | Leu |
| Asp | Thr<br>450 | Gly | Glu | Trp | Pro | Ser<br>455 | Thr | Glu | Pro | Asp | Asp<br>460 | Leu | Asn | Ala | Ile |
| Ala<br>465 | Glu | Ala | Ser | Asn | Thr<br>470 | Gly | Thr | Glu | Ala | Arg<br>475 | Phe | Met | Ala | Leu | Asp<br>480 |
| Gly | Trp | Glu | Ile | Pro<br>485 | Glu | Tyr | Asn | Arg | Thr<br>490 | Trp | Lys | Pro | Glu |

( 2 ) INFORMATION FOR SEQ ID NO:5:

( i ) SEQUENCE CHARACTERISTICS:
        ( A ) LENGTH: 1620 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 136..1617

( x i ) SEQUENCE DESCRIPTION: SEQ ID NO:5:

```
GGATCCTTAG GAATCTAAAC ATTCTGGTTG ACACTCCACA TTTTGAATGT CAGCATTTCG      60

GCCATGGCTG CTATGCAGCC TGTTATTGCA TTTGAAATGG AATAGATCAG CAAACTTATC     120

GGGAGGATGA GTATT ATG ATA ATC AAG GGT AGT GTA CCG GGT AAA GCC GGA     171
                Met Ile Ile Lys Gly Ser Val Pro Gly Lys Ala Gly
                  1               5                  10
```

|     |     |     |     |     |     |     |     |     |     |     |     |     |     |     |     |
|-----|-----|-----|-----|-----|-----|-----|-----|-----|-----|-----|-----|-----|-----|-----|-----|
| GGA | AAA | CCT | CGA | GCG | ACC | ATC | TTT | CAT | AGT | TCT | ATT | GCA | ACG | CTA | CTT | 219 |
| Gly | Lys | Pro<br>15 | Arg | Ala | Thr | Ile | Phe<br>20 | His | Ser | Ser | Ile | Ala<br>25 | Thr | Leu | Leu |
| TTA | ACC | ACA | GTC | TCA | CTG | TCA | GGA | GTA | GCG | CCA | GCA | TTT | GCA | CAG | GCG | 267 |
| Leu | Thr<br>30 | Thr | Val | Ser | Leu | Ser<br>35 | Gly | Val | Ala | Pro | Ala<br>40 | Phe | Ala | Gln | Ala |
| CCG | TCT | GTG | CAC | CAA | CAC | GTC | GCC | TTC | ACT | GAG | GAA | ATT | GGA | GAC | CTT | 315 |
| Pro | Ser | Val | His | Gln | His | Val | Ala | Phe | Thr | Glu | Glu | Ile | Gly | Asp | Leu |
| 45  |     |     |     | 50  |     |     |     |     | 55  |     |     |     |     |     | 60  |
| CCC | GAC | GGC | TCA | AGT | TAC | ATG | ATC | CGT | GTG | CCG | GAG | AAC | TGG | AAC | GGC | 363 |
| Pro | Asp | Gly | Ser | Ser<br>65 | Tyr | Met | Ile | Arg | Val<br>70 | Pro | Glu | Asn | Trp | Asn<br>75 | Gly |
| GTG | TTA | ATT | CGC | GAC | CTA | GAC | CTT | GTC | AGC | GGC | ACC | AGC | AAT | TCT | AAC | 411 |
| Val | Leu | Ile | Arg<br>80 | Asp | Leu | Asp | Leu | Val<br>85 | Ser | Gly | Thr | Ser | Asn<br>90 | Ser | Asn |
| GCC | GCA | AGG | TAC | GAA | ACC | ATG | CTG | AAA | GAA | GGT | TTT | GCC | GTT | GCT | GGC | 459 |
| Ala | Ala | Arg<br>95 | Tyr | Glu | Thr | Met | Leu<br>100 | Lys | Glu | Gly | Phe | Ala<br>105 | Val | Ala | Gly |
| ACG | GCG | AGG | CAT | CCC | CTT | CGG | CAA | TGG | CAA | TAT | GAC | CCC | GCT | CAC | GAG | 507 |
| Thr | Ala | Arg<br>110 | His | Pro | Leu | Arg | Gln<br>115 | Trp | Gln | Tyr | Asp | Pro<br>120 | Ala | His | Glu |
| ATT | GAA | AAC | CTC | AAT | CAC | GTG | CTG | GAC | ACA | TTC | GAG | GAA | AAT | TAC | GGT | 555 |
| Ile | Glu | Asn | Leu | Asn | His | Val | Leu | Asp | Thr | Phe | Glu | Glu | Asn | Tyr | Gly |
| 125 |     |     |     |     | 130 |     |     |     |     | 135 |     |     |     |     | 140 |
| TCA | CCT | GAA | AGA | GTT | ATC | CAG | TAC | GGT | TGC | TCG | GGT | GGG | GCA | CAC | GTG | 603 |
| Ser | Pro | Glu | Arg | Val<br>145 | Ile | Gln | Tyr | Gly | Cys<br>150 | Ser | Gly | Gly | Ala | His<br>155 | Val |
| TCA | CTA | GCC | GTG | GCA | GAG | GAC | TTC | TCG | GAC | CGC | GTA | GAT | GGC | TCA | GTT | 651 |
| Ser | Leu | Ala | Val<br>160 | Ala | Glu | Asp | Phe | Ser<br>165 | Asp | Arg | Val | Asp | Gly<br>170 | Ser | Val |
| GCT | CTA | GCT | GCT | CAT | ACT | CCT | GTC | TGG | ATA | ATG | AAT | TCT | TTC | TTG | GAC | 699 |
| Ala | Leu | Ala | Ala | His | Thr | Pro | Val | Trp | Ile | Met | Asn | Ser | Phe | Leu | Asp |

```
                    175                                  180                                       185
GGA TGG TTT TCG CTG CAG TCT CTG ATC GGC GAG TAC TAT GTA GAA GCT      747
Gly Trp Phe Ser Leu Gln Ser Leu Ile Gly Glu Tyr Tyr Val Glu Ala
    190                     195                     200

GGT CAC GGC CCA CTT TCG GAT CTC GCT ATT ACG AAA CTG CCC AAT GAT      795
Gly His Gly Pro Leu Ser Asp Leu Ala Ile Thr Lys Leu Pro Asn Asp
205                     210                     215                     220

GGT AGC TCT AAT TCG AGC GGT CAT GGA ATG GAA GGA GAT CTT CCT GCC      843
Gly Ser Ser Asn Ser Ser Gly His Gly Met Glu Gly Asp Leu Pro Ala
                    225                     230                     235

GCG TGG CGC AAC GCG TTC ACC GCT GCT AAC GCC ACA CCT GAG GGT CGC      891
Ala Trp Arg Asn Ala Phe Thr Ala Ala Asn Ala Thr Pro Glu Gly Arg
            240                     245                     250

GCA CGC ATG GCA CTA GCC TTT GCG CTC GGT CAG TGG TCT CCG TGG TTG      939
Ala Arg Met Ala Leu Ala Phe Ala Leu Gly Gln Trp Ser Pro Trp Leu
        255                     260                     265

GCC GAC AAC ACG CCC CAA CCT GAT CTC GAT GAT CCT GAG GCC ATC GCG      987
Ala Asp Asn Thr Pro Gln Pro Asp Leu Asp Asp Pro Glu Ala Ile Ala
270                     275                     280

GAT TCC GTA TAT GAG TCT GCC ATG CGA CTT GCA GGA AGC CCT GGG GGA     1035
Asp Ser Val Tyr Glu Ser Ala Met Arg Leu Ala Gly Ser Pro Gly Gly
285                     290                     295                     300

GAA GCG CGC ATA ATG TTC GAG AAC GCC GCT CGA GGG CAA CAG CTC TCT     1083
Glu Ala Arg Ile Met Phe Glu Asn Ala Ala Arg Gly Gln Gln Leu Ser
                    305                     310                     315

TGG AAC GAC GAC ATC GAC TAT GCG GAT TTC TGG GAG AAC TCA AAC CCA     1131
Trp Asn Asp Asp Ile Asp Tyr Ala Asp Phe Trp Glu Asn Ser Asn Pro
                320                     325                     330

GCC ATG AAG AGC GCC GTT CAG GAG CTG TAC GAC ACG GCC GGC CTT GAT     1179
Ala Met Lys Ser Ala Val Gln Glu Leu Tyr Asp Thr Ala Gly Leu Asp
            335                     340                     345

CTG CAG TCC GAT ATA GAA ACG GTA AAT TCC CAG CCA CGC ATA GAG GCA     1227
Leu Gln Ser Asp Ile Glu Thr Val Asn Ser Gln Pro Arg Ile Glu Ala
350                     355                     360

TCG CAG TAT GCG CTC GAC TAC TGG AAC ACG CCA GGT CGC AAT GTC ATT     1275
Ser Gln Tyr Ala Leu Asp Tyr Trp Asn Thr Pro Gly Arg Asn Val Ile
365                     370                     375                     380

GGC GAC CCC GAA GTT CCT GTG CTG CGC CTG CAT ATG ATA GGC GAC TAC     1323
Gly Asp Pro Glu Val Pro Val Leu Arg Leu His Met Ile Gly Asp Tyr
                    385                     390                     395

CAA ATT CCC TAT AGT CTT GTA CAG GGC TAC AGC GAT CTT ATC TCA GAG     1371
Gln Ile Pro Tyr Ser Leu Val Gln Gly Tyr Ser Asp Leu Ile Ser Glu
                400                     405                     410

AAC AAC AAT GAT GAC TTG TAC AGA ACT GCT TTT GTG CAA TCC ACT GGA     1419
Asn Asn Asn Asp Asp Leu Tyr Arg Thr Ala Phe Val Gln Ser Thr Gly
            415                     420                     425

CAC TGC AAT TTC ACA GCT GCA GAA AGT TCC GCT GCG ATT GAG GTC ATG     1467
His Cys Asn Phe Thr Ala Ala Glu Ser Ser Ala Ala Ile Glu Val Met
    430                     435                     440

ATG CAA CGG CTT GAC ACG GGT GAG TGG CCG AGC ACC GAG CCG GAT GAT     1515
Met Gln Arg Leu Asp Thr Gly Glu Trp Pro Ser Thr Glu Pro Asp Asp
445                     450                     455                     460

CTG AAT GCA ATT GCC GAA GCC TCA AAC ACC GGA ACT GAA GCA CGT TTC     1563
Leu Asn Ala Ile Ala Glu Ala Ser Asn Thr Gly Thr Glu Ala Arg Phe
                    465                     470                     475

ATG GCC CTA GAT GGC TGG GAA ATA CCC GAG TAC AAT CGT ACT TGG AAG     1611
Met Ala Leu Asp Gly Trp Glu Ile Pro Glu Tyr Asn Arg Thr Trp Lys
                480                     485                     490

CCT GAA TAA                                                         1620
Pro Glu
```

( 2 ) INFORMATION FOR SEQ ID NO:6:

( i ) SEQUENCE CHARACTERISTICS:
        ( A ) LENGTH: 3029 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 136..1617

( x i ) SEQUENCE DESCRIPTION: SEQ ID NO:6:

```
GGATCCTTAG GAATCTAAAC ATTCTGGTTG ACACTCCACA TTTTGAATGT CAGCATTTCG        60

GCCATGGCTG CTATGCAGCC TGTTATTGCA TTTGAAATGG AATAGATCAG CAAACTTATC       120

GGGAGGATGA GTATT ATG ATA ATC AAG GGT AGT GTA CCG GGT AAA GCC GGA        171
              Met Ile Ile Lys Gly Ser Val Pro Gly Lys Ala Gly
                1               5                  10

GGA AAA CCT CGA GCG ACC ATC TTT CAT AGT TCT ATT GCA ACG CTA CTT         219
Gly Lys Pro Arg Ala Thr Ile Phe His Ser Ser Ile Ala Thr Leu Leu
         15                  20                  25

TTA ACC ACA GTC TCA CTG TCA GGA GTA GCG CCA GCA TTT GCA CAG GCG         267
Leu Thr Thr Val Ser Leu Ser Gly Val Ala Pro Ala Phe Ala Gln Ala
     30                  35                  40

CCG TCT GTG CAC CAA CAC GTC GCC TTC ACT GAG GAA ATT GGA GAC CTT         315
Pro Ser Val His Gln His Val Ala Phe Thr Glu Glu Ile Gly Asp Leu
 45                  50                  55                  60

CCC GAC GGC TCA AGT TAC ATG ATC CGT GTG CCG GAG AAC TGG AAC GGC         363
Pro Asp Gly Ser Ser Tyr Met Ile Arg Val Pro Glu Asn Trp Asn Gly
                 65                  70                  75

GTG TTA ATT CGC GAC CTA GAC CTT GTC AGC GGC ACC AGC AAT TCT AAC         411
Val Leu Ile Arg Asp Leu Asp Leu Val Ser Gly Thr Ser Asn Ser Asn
             80                  85                  90

GCC GCA AGG TAC GAA ACC ATG CTG AAA GAA GGT TTT GCC GTT GCT GGC         459
Ala Ala Arg Tyr Glu Thr Met Leu Lys Glu Gly Phe Ala Val Ala Gly
         95                 100                 105

ACG GCG AGG CAT CCC CTT CGG CAA TGG CAA TAT GAC CCC GCT CAC GAG         507
Thr Ala Arg His Pro Leu Arg Gln Trp Gln Tyr Asp Pro Ala His Glu
    110                 115                 120

ATT GAA AAC CTC AAT CAC GTG CTG GAC ACA TTC GAG GAA AAT TAC GGT         555
Ile Glu Asn Leu Asn His Val Leu Asp Thr Phe Glu Glu Asn Tyr Gly
125                 130                 135                 140

TCA CCT GAA AGA GTT ATC CAG TAC GGT TGC TCG GGT GGG GCA CAC GTG         603
Ser Pro Glu Arg Val Ile Gln Tyr Gly Cys Ser Gly Gly Ala His Val
                145                 150                 155

TCA CTA GCC GTG GCA GAG GAC TTC TCG GAC CGC GTA GAT GGC TCA GTT         651
Ser Leu Ala Val Ala Glu Asp Phe Ser Asp Arg Val Asp Gly Ser Val
            160                 165                 170

GCT CTA GCT GCT CAT ACT CCT GTC TGG ATA ATG AAT TCT TTC TTG GAC         699
Ala Leu Ala Ala His Thr Pro Val Trp Ile Met Asn Ser Phe Leu Asp
        175                 180                 185

GGA TGG TTT TCG CTG CAG TCT CTG ATC GGC GAG TAC TAT GTA GAA GCT         747
Gly Trp Phe Ser Leu Gln Ser Leu Ile Gly Glu Tyr Tyr Val Glu Ala
    190                 195                 200

GGT CAC GGC CCA CTT TCG GAT CTC GCT ATT ACG AAA CTG CCC AAT GAT         795
Gly His Gly Pro Leu Ser Asp Leu Ala Ile Thr Lys Leu Pro Asn Asp
205                 210                 215                 220

GGT AGC TCT AAT TCG AGC GGT CAT GGA ATG GAA GGA GAT CTT CCT GCC         843
Gly Ser Ser Asn Ser Ser Gly His Gly Met Glu Gly Asp Leu Pro Ala
                225                 230                 235

GCG TGG CGC AAC GCG TTC ACC GCT GCT AAC GCC ACA CCT GAG GGT CGC         891
Ala Trp Arg Asn Ala Phe Thr Ala Ala Asn Ala Thr Pro Glu Gly Arg
```

```
                      240                         245                         250
GCA CGC ATG GCA CTA GCC TTT GCG CTC GGT CAG TGG TCT CCG TGG TTG              939
Ala Arg Met Ala Leu Ala Phe Ala Leu Gly Gln Trp Ser Pro Trp Leu
        255                         260                     265

GCC GAC AAC ACG CCC CAA CCT GAT CTC GAT GAT CCT GAG GCC ATC GCG              987
Ala Asp Asn Thr Pro Gln Pro Asp Leu Asp Asp Pro Glu Ala Ile Ala
        270                         275                         280

GAT TCC GTA TAT GAG TCT GCC ATG CGA CTT GCA GGA AGC CCT GGG GGA             1035
Asp Ser Val Tyr Glu Ser Ala Met Arg Leu Ala Gly Ser Pro Gly Gly
285                         290                         295                         300

GAA GCG CGC ATA ATG TTC GAG AAC GCC GCT CGA GGG CAA CAG CTC TCT             1083
Glu Ala Arg Ile Met Phe Glu Asn Ala Ala Arg Gly Gln Gln Leu Ser
                        305                         310                         315

TGG AAC GAC GAC ATC GAC TAT GCG GAT TTC TGG GAG AAC TCA AAC CCA             1131
Trp Asn Asp Asp Ile Asp Tyr Ala Asp Phe Trp Glu Asn Ser Asn Pro
                320                         325                         330

GCC ATG AAG AGC GCC GTT CAG GAG CTG TAC GAC ACG GCC GGC CTT GAT             1179
Ala Met Lys Ser Ala Val Gln Glu Leu Tyr Asp Thr Ala Gly Leu Asp
        335                         340                         345

CTG CAG TCC GAT ATA GAA ACG GTA AAT TCC CAG CCA CGC ATA GAG GCA             1227
Leu Gln Ser Asp Ile Glu Thr Val Asn Ser Gln Pro Arg Ile Glu Ala
        350                         355                         360

TCG CAG TAT GCG CTC GAC TAC TGG AAC ACG CCA GGT CGC AAT GTC ATT             1275
Ser Gln Tyr Ala Leu Asp Tyr Trp Asn Thr Pro Gly Arg Asn Val Ile
365                         370                         375                         380

GGC GAC CCC GAA GTT CCT GTG CTG CGC CTG CAT ATG ATA GGC GAC TAC             1323
Gly Asp Pro Glu Val Pro Val Leu Arg Leu His Met Ile Gly Asp Tyr
                        385                         390                         395

CAA ATT CCC TAT AGT CTT GTA CAG GGC TAC AGC GAT CTT ATC TCA GAG             1371
Gln Ile Pro Tyr Ser Leu Val Gln Gly Tyr Ser Asp Leu Ile Ser Glu
                400                         405                         410

AAC AAC AAT GAT GAC TTG TAC AGA ACT GCT TTT GTG CAA TCC ACT GGA             1419
Asn Asn Asn Asp Asp Leu Tyr Arg Thr Ala Phe Val Gln Ser Thr Gly
        415                         420                         425

CAC TGC AAT TTC ACA GCT GCA GAA AGT TCC GCT GCG ATT GAG GTC ATG             1467
His Cys Asn Phe Thr Ala Ala Glu Ser Ser Ala Ala Ile Glu Val Met
        430                         435                         440

ATG CAA CGG CTT GAC ACG GGT GAG TGG CCG AGC ACC GAG CCG GAT GAT             1515
Met Gln Arg Leu Asp Thr Gly Glu Trp Pro Ser Thr Glu Pro Asp Asp
445                         450                         455                         460

CTG AAT GCA ATT GCC GAA GCC TCA AAC ACC GGA ACT GAA GCA CGT TTC             1563
Leu Asn Ala Ile Ala Glu Ala Ser Asn Thr Gly Thr Glu Ala Arg Phe
                        465                         470                         475

ATG GCC CTA GAT GGC TGG GAA ATA CCC GAG TAC AAT CGT ACT TGG AAG             1611
Met Ala Leu Asp Gly Trp Glu Ile Pro Glu Tyr Asn Arg Thr Trp Lys
                480                         485                         490

CCT GAA TAATCACCAT TCTGGAGGCT CACGTTCGCG AAGGGTTGCG GCGAAGAAAA              1667
Pro Glu
CATGCGCCGC AACCTATCCT CCAAACAAGG GCCAGTTCAA CGACGAACAA GCCAGACCGG           1727
CGCAAGCCGC GCTAATCTAA TTCACCGCTC CAACCCGCGA TCTCGCGACC GCCCGCGCTG           1787
CATGTCGAGC TTCTGTTGCT GCGCCCGCTC AAGCGTATAA TCACGCCGGA TAATCGTTTC           1847
CCGCGCTTTG TTCGTGATCC TTGCAACGTC CTTGATGCGA TCGACGTTAC GGGCTGTCTC           1907
TGAAGGCTGT GAGCGTGTGC GATCAAGCGC CTGATCGATA TCGCGATGAT TGCTTGATCC           1967
GAACCGGATC TGCATAGCCC GGGCAATACG TTTGGCTTCA TCAAGCGCCT GTTTGCCATC           2027
AGCCGTCTTT TCGAGCTGAT CGACAAAGCC CGTCCGTGCC TTCGCATCCT TGATCTGATC           2087
GAGCTGCCTG AGCAGGGTTT CGCTGCGAGG TGAGAGGCCA GGAATCTCGA CGCGATCATT           2147
ATTGTCACGC CGCCATTGTT CGGCTTCCTT TTCCTCGGCA AAGCGCCGCG TCCAGGTCTT           2207
```

```
CCCCGCCGCG  TCCAGATGCG  AACTCATCGC  CTCGGCCCGC  TTGAGGGCAT  TTTTTGCGCT    2267

CGGCATTGGC  ACCGAACAGG  CCGAACTTGC  CGCGCAGCTG  TTGATTTCTG  CTGAGAAGTG    2327

ACCCGGTATT  GGAGTGAACC  CCTGGGACTG  GACCAGCGGG  GAAGAAAAGC  TGATACGCTC    2387

TGTGGGCCTT  GAATGGAGAA  GGTCCATGTC  ACCAAGAGGT  CCCTACCGCC  GTCACTCGAT    2447

GCAGTTCAAG  CGTAAGCGCC  AAGCCTGGCC  CGTCTGGTGA  TGGCTGCCTT  TGAGCGCTAT    2507

CGACACCCCG  GAGTTAGTGA  TGGGTGTCAT  GTTCTATGTC  TGCGACTATG  CCTGCAGATA    2567

GAAGTTTCCA  GTTGATCGAG  GCGGTTCCGG  ATCGGATGGA  GGGCGCTCCG  GTTGCGCGGC    2627

GACGCCGGTG  GTCGGACGCG  TTCAAGGCCG  AGATGGTAGC  GCGCAGCTTC  GAACCTGGAA    2687

CGAATGTGTC  GGCACTGGCG  CGCGAGATCG  GCATCCAGTC  CTCGCAGTTG  TTCGGCTGGC    2747

GCGCCGAGGC  CCTCAAGCGC  GGAGAGGTGG  AAAGGCGCGA  TGTTGATATC  GTTGCAACGC    2807

AAGCCTCTCG  CTTGGTGAGC  GGGACGGTCG  AGATCGCGGT  CAACGACACG  GTGATCCGGG    2867

TCGGCATTGA  TATCGGGGAA  GACCATTTGC  GGCGCGTGAT  CCGCGCTGTG  CGGTCGGCAT    2927

GATCCCTGCG  GGTGTGAAGG  TCTATCTGGC  CAGCCAGCCG  GTAGACTTCA  GGAAAGGTCC    2987

AGACGGCCTT  GTTGGCCTGG  TGCGCGATGC  TGGAGCGGAT  CC                       3029
```

(2) INFORMATION FOR SEQ ID NO:7:

(i) SEQUENCE CHARACTERISTICS:
   (A) LENGTH: 135 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:7:

```
GGATCCTTAG  GAATCTAAAC  ATTCTGGTTG  ACACTCCACA  TTTTGAATGT  CAGCATTTCG     60

GCCATGGCTG  CTATGCAGCC  TGTTATTGCA  TTTGAAATGG  AATAGATCAG  CAAACTTATC    120

GGGAGGATGA  GTATT                                                         135
```

(2) INFORMATION FOR SEQ ID NO:8:

(i) SEQUENCE CHARACTERISTICS:
   (A) LENGTH: 126 base pairs
   (B) TYPE: nucleic acid
   (C) STRANDEDNESS: single
   (D) TOPOLOGY: linear (ii) MOLECULE TYPE: DNA (genomic)

(ix) FEATURE:
   (A) NAME/KEY: CDS
   (B) LOCATION: 1..126

(xi) SEQUENCE DESCRIPTION: SEQ ID NO:8:

```
ATG  ATA  ATC  AAG  GGT  AGT  GTA  CCG  GGT  AAA  GCC  GGA  GGA  AAA  CCT  CGA     48
Met  Ile  Ile  Lys  Gly  Ser  Val  Pro  Gly  Lys  Ala  Gly  Gly  Lys  Pro  Arg
 1                  5                   10                      15

GCG  ACC  ATC  TTT  CAT  AGT  TCT  ATT  GCA  ACG  CTA  CTT  TTA  ACC  ACA  GTC     96
Ala  Thr  Ile  Phe  His  Ser  Ser  Ile  Ala  Thr  Leu  Leu  Leu  Thr  Thr  Val
             20                       25                      30

TCA  CTG  TCA  GGA  GTA  GCG  CCA  GCA  TTT  GCA                                  126
Ser  Leu  Ser  Gly  Val  Ala  Pro  Ala  Phe  Ala
          35                      40
```

(2) INFORMATION FOR SEQ ID NO:9:

(i) SEQUENCE CHARACTERISTICS:
   (A) LENGTH: 42 amino acids
   (B) TYPE: amino acid (D) TOPOLOGY: linear (ii) MOLECULE TYPE: protein (xi) SEQUENCE DESCRIPTION: SEQ ID NO:9:

| Met | Ile | Ile | Lys | Gly | Ser | Val | Pro | Gly | Lys | Ala | Gly | Gly | Lys | Pro | Arg |
|---|---|---|---|---|---|---|---|---|---|---|---|---|---|---|---|
| 1 | | | | 5 | | | | | 10 | | | | | 15 | |

| Ala | Thr | Ile | Phe | His | Ser | Ser | Ile | Ala | Thr | Leu | Leu | Leu | Thr | Thr | Val |
|---|---|---|---|---|---|---|---|---|---|---|---|---|---|---|---|
| | | | | 20 | | | | | 25 | | | | | 30 | |

| Ser | Leu | Ser | Gly | Val | Ala | Pro | Ala | Phe | Ala |
|---|---|---|---|---|---|---|---|---|---|
| | | 35 | | | | | 40 | | |

(2) INFORMATION FOR SEQ ID NO:10:

(i) SEQUENCE CHARACTERISTICS:
 (A) LENGTH: 1409 base pairs
 (B) TYPE: nucleic acid
 (C) STRANDEDNESS: single
 (D) TOPOLOGY: linear (ii) MOLECULE TYPE: DNA (genomic)

(xi) SEQUENCE DESCRIPTION: SEQ ID NO:10:

| TCACCATTCT | GGAGGCTCAC | GTTCGCGAAG | GGTTGCGGCG | AAGAAAACAT | GCGCCGCAAC | 60 |
| CTATCCTCCA | AACAAGGGCC | AGTTCAACGA | CGAACAAGCC | AGACCGGCGC | AAGCCGCGCT | 120 |
| AATCTAATTC | ACCGCTCCAA | CCCGCGATCT | CGCGACCGCC | CGCGCTGCAT | GTCGAGCTTC | 180 |
| TGTTGCTGCG | CCCGCTCAAG | CGTATAATCA | CGCCGGATAA | TCGTTTCCCG | CGCTTTGTTC | 240 |
| GTGATCCTTG | CAACGTCCTT | GATGCGATCG | ACGTTACGGG | CTGTCTCTGA | AGGCTGTGAG | 300 |
| CGTGTGCGAT | CAAGCGCCTG | ATCGATATCG | CGATGATTGC | TTGATCCGAA | CCGGATCTGC | 360 |
| ATAGCCCGGG | CAATACGTTT | GGCTTCATCA | AGCGCCTGTT | TGCCATCAGC | CGTCTTTTCG | 420 |
| AGCTGATCGA | CAAAGCCCGT | CCGTGCCTTC | GCATCCTTGA | TCTGATCGAG | CTGCCTGAGC | 480 |
| AGGGTTTCGC | TGCGAGGTGA | GAGGCCAGGA | ATCTCGACGC | GATCATTATT | GTCACGCCGC | 540 |
| CATTGTTCGG | CTTCCTTTTC | CTCGGCAAAG | CGCCGCGTCC | AGGTCTTCCC | CGCCGCGTCC | 600 |
| AGATGCGAAC | TCATCGCCTC | GGCCCGCTTG | AGGGCATTTT | TTGCGCTCGG | CATTGGCACC | 660 |
| GAACAGGCCG | AACTTGCCGC | GCAGCTGTTG | ATTTCTGCTG | AGAAGTGACC | CGGTATTGGA | 720 |
| GTGAACCCCT | GGGACTGGAC | CAGCGGGGAA | GAAAAGCTGA | TACGCTCTGT | GGGCCTTGAA | 780 |
| TGGAGAAGGT | CCATGTCACC | AAGAGGTCCC | TACCGCCGTC | ACTCGATGCA | GTTCAAGCGT | 840 |
| AAGCGCCAAG | CCTGGCCCGT | CTGGTGATGG | CTGCCTTTGA | GCGCTATCGA | CACCCCGGAG | 900 |
| TTAGTGATGG | GTGTCATGTT | CTATGTCTGC | GACTATGCCT | GCAGATAGAA | GTTTCCAGTT | 960 |
| GATCGAGGCG | GTTCCGGATC | GGATGGAGGG | CGCTCCGGTT | GCGCGGCGAC | GCCGGTGGTC | 1020 |
| GGACGCGTTC | AAGGCCGAGA | TGGTAGCGCG | CAGCTTCGAA | CCTGGAACGA | ATGTGTCGGC | 1080 |
| ACTGGCGCGC | GAGATCGGCA | TCCAGTCCTC | GCAGTTGTTC | GGCTGGCGCG | CCGAGGCCCT | 1140 |
| CAAGCGCGGA | GAGGTGGAAA | GGCGCGATGT | TGATATCGTT | GCAACGCAAG | CCTCTCGCTT | 1200 |
| GGTGAGCGGG | ACGGTCGAGA | TCGCGGTCAA | CGACACGGTG | ATCCGGGTCG | GCATTGATAT | 1260 |
| CGGGGAAGAC | CATTTGCGGC | GCGTGATCCG | CGCTGTGCGG | TCGGCATGAT | CCCTGCGGGT | 1320 |
| GTGAAGGTCT | ATCTGGCCAG | CCAGCCGGTA | GACTTCAGGA | AAGGTCCAGA | CGGCCTTGTT | 1380 |
| GGCCTGGTGC | GCGATGCTGG | AGCGGATCC | | | | 1409 |

(2) INFORMATION FOR SEQ ID NO:11:

(i) SEQUENCE CHARACTERISTICS:
 (A) LENGTH: 1362 base pairs
 (B) TYPE: nucleic acid (C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..1359

(xi) SEQUENCE DESCRIPTION: SEQ ID NO:11:

| | | | | | | | | | | | | | | | | |
|---|---|---|---|---|---|---|---|---|---|---|---|---|---|---|---|---|
| ATG | CAG | GCG | CCG | TCT | GTG | CAC | CAA | CAC | GTC | GCC | TTC | ACT | GAG | GAA | ATT | 48 |
| Met | Gln | Ala | Pro | Ser | Val | His | Gln | His | Val | Ala | Phe | Thr | Glu | Glu | Ile | |
| 1 | | | | 5 | | | | | 10 | | | | | | 15 | |
| GGA | GAC | CTT | CCC | GAC | GGC | TCA | AGT | TAC | ATG | ATC | CGT | GTG | CCG | GAG | AAC | 96 |
| Gly | Asp | Leu | Pro | Asp | Gly | Ser | Ser | Tyr | Met | Ile | Arg | Val | Pro | Glu | Asn | |
| | | | 20 | | | | | 25 | | | | | 30 | | | |
| TGG | AAC | GGC | GTG | TTA | ATT | CGC | GAC | CTA | GAC | CTT | GTC | AGC | GGC | ACC | AGC | 144 |
| Trp | Asn | Gly | Val | Leu | Ile | Arg | Asp | Leu | Asp | Leu | Val | Ser | Gly | Thr | Ser | |
| | | 35 | | | | | 40 | | | | | 45 | | | | |
| AAT | TCT | AAC | GCC | GCA | AGG | TAC | GAA | ACC | ATG | CTG | AAA | GAA | GGT | TTT | GCC | 192 |
| Asn | Ser | Asn | Ala | Ala | Arg | Tyr | Glu | Thr | Met | Leu | Lys | Glu | Gly | Phe | Ala | |
| | 50 | | | | | 55 | | | | | 60 | | | | | |
| GTT | GCT | GGC | ACG | GCG | AGG | CAT | CCC | CTT | CGG | CAA | TGG | CAA | TAT | GAC | CCC | 240 |
| Val | Ala | Gly | Thr | Ala | Arg | His | Pro | Leu | Arg | Gln | Trp | Gln | Tyr | Asp | Pro | |
| 65 | | | | | 70 | | | | | 75 | | | | | 80 | |
| GCT | CAC | GAG | ATT | GAA | AAC | CTC | AAT | CAC | GTG | CTG | GAC | ACA | TTC | GAG | GAA | 288 |
| Ala | His | Glu | Ile | Glu | Asn | Leu | Asn | His | Val | Leu | Asp | Thr | Phe | Glu | Glu | |
| | | | | 85 | | | | | 90 | | | | | 95 | | |
| AAT | TAC | GGT | TCA | CCT | GAA | AGA | GTT | ATC | CAG | TAC | GGT | TGC | TCG | GGT | GGG | 336 |
| Asn | Tyr | Gly | Ser | Pro | Glu | Arg | Val | Ile | Gln | Tyr | Gly | Cys | Ser | Gly | Gly | |
| | | | 100 | | | | | 105 | | | | | 110 | | | |
| GCA | CAC | GTG | TCA | CTA | GCC | GTG | GCA | GAG | GAC | TTC | TCG | GAC | CGC | GTA | GAT | 384 |
| Ala | His | Val | Ser | Leu | Ala | Val | Ala | Glu | Asp | Phe | Ser | Asp | Arg | Val | Asp | |
| | | 115 | | | | | 120 | | | | | 125 | | | | |
| GGC | TCA | GTT | GCT | CTA | GCT | GCT | CAT | ACT | CCT | GTC | TGG | ATA | ATG | AAT | TCT | 432 |
| Gly | Ser | Val | Ala | Leu | Ala | Ala | His | Thr | Pro | Val | Trp | Ile | Met | Asn | Ser | |
| | 130 | | | | | 135 | | | | | 140 | | | | | |
| TTC | TTG | GAC | GGA | TGG | TTT | TCG | CTG | CAG | TCT | CTG | ATC | GGC | GAG | TAC | TAT | 480 |
| Phe | Leu | Asp | Gly | Trp | Phe | Ser | Leu | Gln | Ser | Leu | Ile | Gly | Glu | Tyr | Tyr | |
| 145 | | | | | 150 | | | | | 155 | | | | | 160 | |
| GTA | GAA | GCT | GGT | CAC | GGC | CCA | CTT | TCG | GAT | CTC | GCT | ATT | ACG | AAA | CTG | 528 |
| Val | Glu | Ala | Gly | His | Gly | Pro | Leu | Ser | Asp | Leu | Ala | Ile | Thr | Lys | Leu | |
| | | | | 165 | | | | | 170 | | | | | 175 | | |
| CCC | AAT | GAT | GGT | AGC | TCT | AAT | TCG | AGC | GGT | CAT | GGA | ATG | GAA | GGA | GAT | 576 |
| Pro | Asn | Asp | Gly | Ser | Ser | Asn | Ser | Ser | Gly | His | Gly | Met | Glu | Gly | Asp | |
| | | | 180 | | | | | 185 | | | | | 190 | | | |
| CTT | CCT | GCC | GCG | TGG | CGC | AAC | GCG | TTC | ACC | GCT | GCT | AAC | GCC | ACA | CCT | 624 |
| Leu | Pro | Ala | Ala | Trp | Arg | Asn | Ala | Phe | Thr | Ala | Ala | Asn | Ala | Thr | Pro | |
| | | 195 | | | | | 200 | | | | | 205 | | | | |
| GAG | GGT | CGC | GCA | CGC | ATG | GCA | CTA | GCC | TTT | GCG | CTC | GGT | CAG | TGG | TCT | 672 |
| Glu | Gly | Arg | Ala | Arg | Met | Ala | Leu | Ala | Phe | Ala | Leu | Gly | Gln | Trp | Ser | |
| | 210 | | | | | 215 | | | | | 220 | | | | | |
| CCG | TGG | TTG | GCC | GAC | AAC | ACG | CCC | CAA | CCT | GAT | CTC | GAT | GAT | CCT | GAG | 720 |
| Pro | Trp | Leu | Ala | Asp | Asn | Thr | Pro | Gln | Pro | Asp | Leu | Asp | Asp | Pro | Glu | |
| 225 | | | | | 230 | | | | | 235 | | | | | 240 | |
| GCC | ATC | GCG | GAT | TCC | GTA | TAT | GAG | TCT | GCC | ATG | CGA | CTT | GCA | GGA | AGC | 768 |
| Ala | Ile | Ala | Asp | Ser | Val | Tyr | Glu | Ser | Ala | Met | Arg | Leu | Ala | Gly | Ser | |
| | | | | 245 | | | | | 250 | | | | | 255 | | |
| CCT | GGG | GGA | GAA | GCG | CGC | ATA | ATG | TTC | GAG | AAC | GCC | GCT | CGA | GGG | CAA | 816 |
| Pro | Gly | Gly | Glu | Ala | Arg | Ile | Met | Phe | Glu | Asn | Ala | Ala | Arg | Gly | Gln | |
| | | | 260 | | | | | 265 | | | | | 270 | | | |
| CAG | CTC | TCT | TGG | AAC | GAC | GAC | ATC | GAC | TAT | GCG | GAT | TTC | TGG | GAG | AAC | 864 |
| Gln | Leu | Ser | Trp | Asn | Asp | Asp | Ile | Asp | Tyr | Ala | Asp | Phe | Trp | Glu | Asn | |
| | | 275 | | | | | 280 | | | | | 285 | | | | |

| | | | | | | | | | | | | | | | | |
|---|---|---|---|---|---|---|---|---|---|---|---|---|---|---|---|---|
| TCA | AAC | CCA | GCC | ATG | AAG | AGC | GCC | GTT | CAG | GAG | CTG | TAC | GAC | ACG | GCC | 912 |
| Ser | Asn | Pro | Ala | Met | Lys | Ser | Ala | Val | Gln | Glu | Leu | Tyr | Asp | Thr | Ala | |
| | 290 | | | | 295 | | | | | 300 | | | | | | |
| GGC | CTT | GAT | CTG | CAG | TCC | GAT | ATA | GAA | ACG | GTA | AAT | TCC | CAG | CCA | CGC | 960 |
| Gly | Leu | Asp | Leu | Gln | Ser | Asp | Ile | Glu | Thr | Val | Asn | Ser | Gln | Pro | Arg | |
| 305 | | | | | 310 | | | | | 315 | | | | | 320 | |
| ATA | GAG | GCA | TCG | CAG | TAT | GCG | CTC | GAC | TAC | TGG | AAC | ACG | CCA | GGT | CGC | 1008 |
| Ile | Glu | Ala | Ser | Gln | Tyr | Ala | Leu | Asp | Tyr | Trp | Asn | Thr | Pro | Gly | Arg | |
| | | | | 325 | | | | | 330 | | | | | 335 | | |
| AAT | GTC | ATT | GGC | GAC | CCC | GAA | GTT | CCT | GTG | CTG | CGC | CTG | CAT | ATG | ATA | 1056 |
| Asn | Val | Ile | Gly | Asp | Pro | Glu | Val | Pro | Val | Leu | Arg | Leu | His | Met | Ile | |
| | | | 340 | | | | 345 | | | | | 350 | | | | |
| GGC | GAC | TAC | CAA | ATT | CCC | TAT | AGT | CTT | GTA | CAG | GGC | TAC | AGC | GAT | CTT | 1104 |
| Gly | Asp | Tyr | Gln | Ile | Pro | Tyr | Ser | Leu | Val | Gln | Gly | Tyr | Ser | Asp | Leu | |
| | | 355 | | | | | 360 | | | | | 365 | | | | |
| ATC | TCA | GAG | AAC | AAC | AAT | GAT | GAC | TTG | TAC | AGA | ACT | GCT | TTT | GTG | CAA | 1152 |
| Ile | Ser | Glu | Asn | Asn | Asn | Asp | Asp | Leu | Tyr | Arg | Thr | Ala | Phe | Val | Gln | |
| | 370 | | | | | 375 | | | | | 380 | | | | | |
| TCC | ACT | GGA | CAC | TGC | AAT | TTC | ACA | GCT | GCA | GAA | AGT | TCC | GCT | GCG | ATT | 1200 |
| Ser | Thr | Gly | His | Cys | Asn | Phe | Thr | Ala | Ala | Glu | Ser | Ser | Ala | Ala | Ile | |
| 385 | | | | | 390 | | | | | 395 | | | | | 400 | |
| GAG | GTC | ATG | ATG | CAA | CGG | CTT | GAC | ACG | GGT | GAG | TGG | CCG | AGC | ACC | GAG | 1248 |
| Glu | Val | Met | Met | Gln | Arg | Leu | Asp | Thr | Gly | Glu | Trp | Pro | Ser | Thr | Glu | |
| | | | | 405 | | | | | 410 | | | | | 415 | | |
| CCG | GAT | GAT | CTG | AAT | GCA | ATT | GCC | GAA | GCC | TCA | AAC | ACC | GGA | ACT | GAA | 1296 |
| Pro | Asp | Asp | Leu | Asn | Ala | Ile | Ala | Glu | Ala | Ser | Asn | Thr | Gly | Thr | Glu | |
| | | | 420 | | | | 425 | | | | | 430 | | | | |
| GCA | CGT | TTC | ATG | GCC | CTA | GAT | GGC | TGG | GAA | ATA | CCC | GAG | TAC | AAT | CGT | 1344 |
| Ala | Arg | Phe | Met | Ala | Leu | Asp | Gly | Trp | Glu | Ile | Pro | Glu | Tyr | Asn | Arg | |
| | | 435 | | | | | 440 | | | | | 445 | | | | |
| ACT | TGG | AAG | CCT | GAA | TAA | | | | | | | | | | | 1362 |
| Thr | Trp | Lys | Pro | Glu | | | | | | | | | | | | |
| | | 450 | | | | | | | | | | | | | | |

( 2 ) INFORMATION FOR SEQ ID NO:12:

( i ) SEQUENCE CHARACTERISTICS:
        ( A ) LENGTH: 453 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Gln | Ala | Pro | Ser | Val | His | Gln | His | Val | Ala | Phe | Thr | Glu | Glu | Ile |
| 1 | | | | 5 | | | | | 10 | | | | | 15 | |
| Gly | Asp | Leu | Pro | Asp | Gly | Ser | Ser | Tyr | Met | Ile | Arg | Val | Pro | Glu | Asn |
| | | | 20 | | | | | 25 | | | | | 30 | | |
| Trp | Asn | Gly | Val | Leu | Ile | Arg | Asp | Leu | Asp | Leu | Val | Ser | Gly | Thr | Ser |
| | | 35 | | | | | 40 | | | | | 45 | | | |
| Asn | Ser | Asn | Ala | Ala | Arg | Tyr | Glu | Thr | Met | Leu | Lys | Glu | Gly | Phe | Ala |
| | 50 | | | | | 55 | | | | | 60 | | | | |
| Val | Ala | Gly | Thr | Ala | Arg | His | Pro | Leu | Arg | Gln | Trp | Gln | Tyr | Asp | Pro |
| 65 | | | | | 70 | | | | | 75 | | | | | 80 |
| Ala | His | Glu | Ile | Glu | Asn | Leu | Asn | His | Val | Leu | Asp | Thr | Phe | Glu | Glu |
| | | | | 85 | | | | | 90 | | | | | 95 | |
| Asn | Tyr | Gly | Ser | Pro | Glu | Arg | Val | Ile | Gln | Tyr | Gly | Cys | Ser | Gly | Gly |
| | | | 100 | | | | | 105 | | | | | 110 | | |
| Ala | His | Val | Ser | Leu | Ala | Val | Ala | Glu | Asp | Phe | Ser | Asp | Arg | Val | Asp |
| | | 115 | | | | | 120 | | | | | 125 | | | |
| Gly | Ser | Val | Ala | Leu | Ala | Ala | His | Thr | Pro | Val | Trp | Ile | Met | Asn | Ser |

130                          135                          140
Phe  Leu  Asp  Gly  Trp  Phe  Ser  Leu  Gln  Ser  Leu  Ile  Gly  Glu  Tyr  Tyr
145                      150                      155                      160
Val  Glu  Ala  Gly  His  Gly  Pro  Leu  Ser  Asp  Leu  Ala  Ile  Thr  Lys  Leu
                    165                      170                      175
Pro  Asn  Asp  Gly  Ser  Ser  Asn  Ser  Ser  Gly  His  Gly  Met  Glu  Gly  Asp
               180                      185                      190
Leu  Pro  Ala  Ala  Trp  Arg  Asn  Ala  Phe  Thr  Ala  Ala  Asn  Ala  Thr  Pro
          195                      200                      205
Glu  Gly  Arg  Ala  Arg  Met  Ala  Leu  Ala  Phe  Ala  Leu  Gly  Gln  Trp  Ser
     210                      215                      220
Pro  Trp  Leu  Ala  Asp  Asn  Thr  Pro  Gln  Pro  Asp  Leu  Asp  Asp  Pro  Glu
225                      230                      235                      240
Ala  Ile  Ala  Asp  Ser  Val  Tyr  Glu  Ser  Ala  Met  Arg  Leu  Ala  Gly  Ser
                    245                      250                      255
Pro  Gly  Gly  Glu  Ala  Arg  Ile  Met  Phe  Glu  Asn  Ala  Ala  Arg  Gly  Gln
               260                      265                      270
Gln  Leu  Ser  Trp  Asn  Asp  Ile  Asp  Tyr  Ala  Asp  Phe  Trp  Glu  Asn
          275                      280                      285
Ser  Asn  Pro  Ala  Met  Lys  Ser  Ala  Val  Gln  Glu  Leu  Tyr  Asp  Thr  Ala
     290                      295                      300
Gly  Leu  Asp  Leu  Gln  Ser  Asp  Ile  Glu  Thr  Val  Asn  Ser  Gln  Pro  Arg
305                      310                      315                      320
Ile  Glu  Ala  Ser  Gln  Tyr  Ala  Leu  Asp  Tyr  Trp  Asn  Thr  Pro  Gly  Arg
                    325                      330                      335
Asn  Val  Ile  Gly  Asp  Pro  Glu  Val  Pro  Val  Leu  Arg  Leu  His  Met  Ile
               340                      345                      350
Gly  Asp  Tyr  Gln  Ile  Pro  Tyr  Ser  Leu  Val  Gln  Gly  Tyr  Ser  Asp  Leu
          355                      360                      365
Ile  Ser  Glu  Asn  Asn  Asn  Asp  Leu  Tyr  Arg  Thr  Ala  Phe  Val  Gln
     370                      375                      380
Ser  Thr  Gly  His  Cys  Asn  Phe  Thr  Ala  Ala  Glu  Ser  Ser  Ala  Ala  Ile
385                      390                      395                      400
Glu  Val  Met  Met  Gln  Arg  Leu  Asp  Thr  Gly  Glu  Trp  Pro  Ser  Thr  Glu
                    405                      410                      415
Pro  Asp  Asp  Leu  Asn  Ala  Ile  Ala  Glu  Ala  Ser  Asn  Thr  Gly  Thr  Glu
               420                      425                      430
Ala  Arg  Phe  Met  Ala  Leu  Asp  Gly  Trp  Glu  Ile  Pro  Glu  Tyr  Asn  Arg
          435                      440                      445
Thr  Trp  Lys  Pro  Glu
450

4. The phthalyl amidase of claim 1, having the amino acid sequence of SEQ ID: 2.

5. The phthalyl amidase of claim 1, having the amino acid sequence of SEQ ID: 4.

* * * * *